(12) United States Patent
Gupta et al.

(10) Patent No.: US 11,267,951 B2
(45) Date of Patent: Mar. 8, 2022

(54) STABILIZER COMPOSITIONS CONTAINING SUBSTITUTED CHROMAN COMPOUNDS AND METHODS OF USE

(75) Inventors: Ram Gupta, Stamford, CT (US);
Sari-Beth Samuels, Ramsey, NJ (US);
J. Mon Hei Eng, Wilton, CT (US);
Thomas Steele, Milford, CT (US)

(73) Assignee: CYTEC TECHNOLOGY CORP., Princeton, NJ (US)

(*) Notice: Subject to any disclaimer, the term of this patent is extended or adjusted under 35 U.S.C. 154(b) by 643 days.

(21) Appl. No.: 13/495,109

(22) Filed: Jun. 13, 2012

(65) Prior Publication Data

US 2013/0145962 A1 Jun. 13, 2013

Related U.S. Application Data

(63) Continuation-in-part of application No. 13/323,173, filed on Dec. 12, 2011.

(60) Provisional application No. 61/422,255, filed on Dec. 13, 2010.

(51) Int. Cl.
| | |
|---|---|
| C08K 5/00 | (2006.01) |
| C07D 311/72 | (2006.01) |
| C08K 5/1545 | (2006.01) |
| B29C 41/04 | (2006.01) |
| C08K 5/51 | (2006.01) |
| C08L 23/08 | (2006.01) |
| C08L 23/10 | (2006.01) |
| C08K 5/34 | (2006.01) |
| C08L 23/12 | (2006.01) |
| B29K 23/00 | (2006.01) |

(52) U.S. Cl.
CPC .............. *C08K 5/005* (2013.01); *B29C 41/04* (2013.01); *C07D 311/72* (2013.01); *C08K 5/00* (2013.01); *C08K 5/1545* (2013.01); *C08K 5/34* (2013.01); *C08K 5/51* (2013.01); *C08L 23/0815* (2013.01); *C08L 23/10* (2013.01); *C08L 23/12* (2013.01); *B29K 2023/12* (2013.01)

(58) Field of Classification Search
CPC ....... C08L 23/12; C08K 5/005; C07D 311/72; B29K 2023/12
USPC .................................................. 264/310, 311
See application file for complete search history.

(56) References Cited

U.S. PATENT DOCUMENTS

| | | | |
|---|---|---|---|
| 4,240,961 A | 12/1980 | Lai | |
| 4,325,863 A | 4/1982 | Hinsken et al. | |
| 4,338,244 A | 7/1982 | Hinsken et al. | |
| 4,480,092 A | 10/1984 | Lai et al. | |
| 4,489,099 A | 12/1984 | Shaheen et al. | |
| 4,629,752 A | 12/1986 | Layer et al. | |
| 4,639,479 A | 1/1987 | Lai et al. | |
| 4,694,090 A * | 9/1987 | Shiono | C07D 311/72 549/389 |
| 4,806,580 A | 2/1989 | Bock et al. | |
| 4,925,888 A | 5/1990 | Aumueller et al. | |
| 5,013,836 A | 5/1991 | Lai | |
| 5,175,312 A | 12/1992 | Dubs et al. | |
| 5,216,052 A | 6/1993 | Nesvadba et al. | |
| 5,218,008 A * | 6/1993 | Parrish | C08K 5/1545 521/114 |
| 5,252,643 A | 10/1993 | Nesvadba | |
| 5,308,549 A | 5/1994 | Laermer et al. | |
| 5,310,771 A | 5/1994 | Walters | |
| 5,356,966 A | 10/1994 | Nesvadba | |
| 5,357,020 A * | 10/1994 | Cogen | C08G 77/14 528/27 |
| 5,367,008 A | 11/1994 | Nesvadba | |
| 5,369,159 A | 11/1994 | Nesvadba | |
| 5,426,141 A | 6/1995 | Akao | |
| 5,428,162 A | 6/1995 | Nesvadba | |
| 5,428,177 A | 6/1995 | Nesvadba | |
| 5,488,117 A | 1/1996 | Nesvadba | |
| 5,516,920 A | 5/1996 | Nesvadba et al. | |
| H1600 H * | 10/1996 | Imfeld | 524/100 |

(Continued)

FOREIGN PATENT DOCUMENTS

| | | |
|---|---|---|
| CA | 1241009 A | 8/1988 |
| EP | 0682073 A2 | 11/1995 |

(Continued)

OTHER PUBLICATIONS

James H. Botkin et al., "An Additive Approach to Cycle Time Reduction in Rotational Molding;" Society of Plastics Engineers, Rotomolding Conference, Session 2, 2004.
International Search Report of International Application No. PCT/US2011/064320, dated Jun. 8, 2012.
Written Opinion of International Application No. PCT/US2011/064320, dated Jun. 8, 2012.
Laermer and Zambetti, "Alpha-Tocopherol (Vitamin E)—the Natural Antioxidant for Polyolefins;" Journal of Plastic Film and Sheeting; 1992; V-8; pp. 228-248.

(Continued)

*Primary Examiner* — Atul P. Khare
(74) *Attorney, Agent, or Firm* — Dennis J. Jakiela; Charles E. Bell, Esq.

(57) ABSTRACT

Stabilizer compositions having a chroman-based compound according to Formula (V):

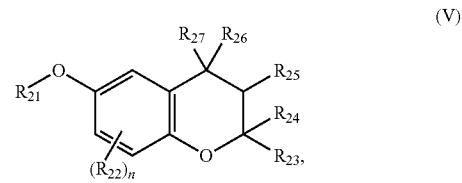

and their use in processes for stabilizing organic materials subject to degradation and/or discoloration due to the effects from light, oxygen and heat, and in processes for producing articles from organic materials blended therewith, are provided herein.

13 Claims, 3 Drawing Sheets

(56) References Cited

U.S. PATENT DOCUMENTS

| | | |
|---|---|---|
| 5,594,055 A | 1/1997 | Young |
| 5,747,568 A | 5/1998 | Fischer et al. |
| 5,807,504 A | 9/1998 | Krockenberger et al. |
| 5,837,759 A | 11/1998 | Trauth et al. |
| 5,844,027 A | 12/1998 | Burdick et al. |
| 5,883,165 A | 3/1999 | Krohnke et al. |
| 6,022,915 A | 2/2000 | Ticktin et al. |
| 6,051,164 A | 4/2000 | Samuels |
| 6,056,897 A | 5/2000 | Pallini et al. |
| 6,271,377 B1 | 8/2001 | Galbo et al. |
| 6,444,733 B1 | 9/2002 | Stadler |
| 6,465,548 B1 | 10/2002 | Inoue et al. |
| 6,468,258 B1 | 10/2002 | Shang |
| 6,492,442 B1 | 12/2002 | Appel et al. |
| 6,541,547 B1 | 4/2003 | Schmutz et al. |
| 6,843,939 B2 | 1/2005 | Stretanski et al. |
| 6,902,695 B2 | 6/2005 | Stadler |
| 7,109,259 B2 | 9/2006 | Lazzari et al. |
| 7,144,919 B1 | 12/2006 | Kim et al. |
| 7,307,126 B2 | 12/2007 | Lustiger et al. |
| 7,375,149 B2 * | 5/2008 | Rotzinger ............. C08K 5/005 524/110 |
| 8,044,161 B2 | 10/2011 | Tiitinen et al. |
| 8,173,753 B2 * | 5/2012 | Nagano ................ C08G 63/80 502/168 |
| 2005/0004275 A1 | 1/2005 | Heidenfelder et al. |
| 2006/0167146 A1 | 7/2006 | Rotzinger et al. |
| 2007/0227087 A1 | 10/2007 | Nasr et al. |
| 2007/0256352 A1 | 11/2007 | Wood et al. |
| 2009/0085252 A1 | 4/2009 | Minder et al. |
| 2010/0036079 A1 | 2/2010 | Tiitinen et al. |
| 2010/0249945 A1 * | 9/2010 | Yakimicki ............. A61L 27/16 623/23.59 |
| 2010/0266798 A1 | 10/2010 | Anker et al. |
| 2010/0327487 A1 | 12/2010 | Yu et al. |
| 2011/0272648 A1 | 11/2011 | Fukushima et al. |
| 2012/0146257 A1 | 6/2012 | Eng et al. |

FOREIGN PATENT DOCUMENTS

| | | | |
|---|---|---|---|
| EP | 0860467 A1 | 8/1998 | |
| EP | 0889085 B1 | 7/2002 | |
| EP | 1308084 A1 | 5/2003 | |
| EP | 2014704 B1 | 1/2009 | |
| JP | 5455043 A | 5/1979 | |
| JP | 54055043 A * | 5/1979 | |
| JP | 58096638 A * | 6/1983 | |
| JP | S5896638 A | 6/1983 | |
| JP | 01170632 A * | 7/1989 | |
| JP | H01170632 | 7/1989 | |
| JP | 2001212837 A | 8/2001 | |
| JP | 2011153251 A | 8/2011 | |
| WO | 198808863 A1 | 11/1988 | |
| WO | 1990007547 A1 | 7/1990 | |
| WO | 1997003974 A2 | 2/1997 | |
| WO | 1997049758 A1 | 12/1997 | |
| WO | 2004024810 A2 | 3/2004 | |
| WO | WO 2007088130 A1 * | 8/2007 | ........... B29C 41/003 |
| WO | 2007104689 A1 | 9/2007 | |
| WO | 2008124825 A2 | 10/2008 | |
| WO | 2009007265 A1 | 1/2009 | |
| WO | WO-2009142196 A1 * | 11/2009 | ............. C08G 63/87 |

OTHER PUBLICATIONS

International Preliminary Report on Patentability of International Application No. PCT/US2013/045318; dated Aug. 7, 2013.
International Search Report of International Application No. PCT/US2013/045318; dated Aug. 7, 2013.
Huang et al "Comparison of free radical formation induced by baicalein and pentamethyl-hydroxychromane in human promyelocytic leukemia cells using electron spin resource"; Journal of Food and Drug Analysis 22; 2014; pp. 379-390.
International Preliminary Report on Patentability; International Application No. PCT/US2011/064320; International Filing Date Dec. 12, 2011; dated Jun. 18, 2013; 6 pages.
Machine Translation for JP2011153251.
Office Action for U.S. Appl. No. 13/323,173 dated Apr. 3, 2015.
Office Action for U.S. Appl. No. 13/323,173 dated Dec. 10, 2015.
Office Action for U.S. Appl. No. 13/323,173 dated Mar. 13, 2017.
Office Action for U.S. Appl. No. 13/323,173 dated Jul. 22, 2016.
Office Action for U.S. Appl. No. 13/323,173 dated Sep. 28, 2017.
Partial Translation for JPH01170632.
Partial Translation for JPS58096638.
Written Opinion of the International Searching Authority; International Application No. PCT/US2013/045318; International Filign Date Jun. 12, 2013; dated Aug. 7, 2013; 5 pages.
Chap. 3, 'PVC Stabilizers and Plasticizers', In Zweifel, Maier, Schiller, Ed. 'Plastics Additives Handbook', 6th Ed, pp. 425-433.
Examiner Interview Summary for U.S. Appl. No. 13/323,173 dated Dec. 10, 2020.
"Metallocene Polyethylene Films." Brentwood Plastics, retrieved from https://www.brentwoodplastics.com/metallocene on Feb. 4, 2021.
Office Action for U.S. Appl. No. 13/323,173 dated Dec. 18, 2020.
Office Action for U.S. Appl. No. 13/323,173 dated Jun. 30, 2020.
Office Action for U.S. Appl. No. 13/323,173 dated Jan. 17, 2020.
Office Action for U.S. Appl. No. 13/323,173 dated Apr. 27, 2018.
Van Henegouwen et al., J. Photochem. and Photobio, 29, 1995, pp. 45-51.

* cited by examiner

STABILIZER COMPOSITIONS CONTAINING SUBSTITUTED CHROMAN COMPOUNDS AND METHODS OF USE

CROSS-REFERENCE TO RELATED APPLICATIONS

This application is a continuation-in-part of U.S. application Ser. No. 13/323,173 filed Dec. 12, 2011, which claims priority benefit of U.S. Provisional Application No. 61/422,255 filed Dec. 13, 2010, each of which is incorporated herein by reference in its entirety.

BACKGROUND OF THE INVENTION

1. Field of the Invention

The invention described herein relates to stabilizer compositions for nonliving organic materials. More particularly, the invention relates to stabilizer compositions having certain substituted chroman compounds and, if desired, other additives for stabilizing nonliving organic materials against the action of light, oxygen, and/or heat, thereby improving the color, performance, and/or processing of such materials, including plastics.

2. Description of the Related Art

The mechanical, chemical, and/or aesthetic properties of nonliving organic material, e.g., plastics and coating materials, are known to be impaired by the effects of light, oxygen, and heat. For such polymeric materials, this impairment is typically manifested as yellowing or other discoloration, cracking or embrittlement of the material, and/or loss of gloss. Additionally, such polymeric organic materials are subjected to high temperatures and pressures during processing into articles, which can adversely impact the physical properties and/or characteristics, as well as the appearance, of the finished articles made from such materials.

Accordingly, such materials require the addition of various additive systems thereto in order both to be processed and to retain long term stability in order to retain desired service properties. A wide variety of substances are known in the art for use as such additives and stabilizers. In many instances, a mixture of such additives is employed. Known stabilizers include, for example, sterically hindered amines such as Hindered Amine Light Stabilizers (HALS), ultraviolet (UV) light absorbers, and antioxidants.

While some stabilization of organic materials is achieved by using one or more of these classes of compounds with a variety of other additives, the high concentrations required for effective protection often leads to undesirable changes in the properties of the material being stabilized, as well as to compatibility problems, which include exudation, chalking, formation of coatings, or color changes. Stabilizers such as antioxidants traditionally include sterically hindered phenolics, aromatic amines, organo-phosphites/phosphonites, and/or thioethers. However, appropriate combinations of stabilizers have to be carefully selected based on the desired final properties the end article should have.

For example, the prior art is replete with examples of stabilizer compositions for organic polymers containing 6-hydroxychroman compounds including α-tocopherols, alone or in combination with other additives such as phenolics and/or organo-phosphites/phosphonites. Aside from its inherent safety (it is edible and generally recognized as safe ("GRAS")) and its suitable physical properties, α-tocopherol is an effective scavenger of oxy radicals. It is also very reactive toward less electrophilic radicals such as alkyl, toward hydroperoxides, excited states of ketones, ozone, peroxide, nitrogen oxides, and other reactive species associated with oxidative damage. However, despite its recognition as an excellent processing stabilizer and color stabilizer, it is inherently viscous and a dark amber oil that is known to lead to discoloring of organic polymers. As noted by Laermer and Zambetti in Alpha-Tocopherol (Vitamin E)—the Natural Antioxidant for Polyolefins, *Journal of Plastic Film and Sheeting* 1992 8:228-248, 247 α-tocopherol is a suitable stabilizing agent if polymer color is not critical.

Other prior art references detail similar issues with using α-tocopherols in organic polymer materials. U.S. Pat. No. 4,806,580 details the unsuitability of using α-tocopherols for stabilizing colorless plastics (alone or in combination with other additives) as they give rise to discoloration.

U.S. Pat. No. 5,807,504 details stabilizer mixtures of chroman derivatives and organic phosphites or phosphonites, but that they are disadvantageous for being unstable upon storage and after incorporation into the material being stabilized.

U.S. Pat. No. 6,465,548 details that 6-hydroxychroman compounds have not been widely used as antioxidants for purposes of stabilizing organic polymer materials because its marked coloring of these materials has not been overcome.

Accordingly, stabilizer compositions for use in minimizing the effects of light, oxygen, and/or heat in nonliving organic materials require further improvement. Thus, stabilizer compositions and processes that specifically enhance the color, performance, and/or processing of such materials, while simultaneously permitting higher processing temperatures and/or shorter cooling times, and faster injection speeds for high speed molding or that effectively reduce the molding cycle times would be a useful advance in the field and would find rapid acceptance in the chemical additives and various industrial molding industries.

SUMMARY OF THE INVENTION

As described in detail hereinbelow, the inventors have discovered stabilizer compositions that enhance the characteristics and performance of nonliving organic materials against the deleterious effects of light, oxygen, and/or heat, as well as the use of these compositions for reducing cycle time in various molding processes related to polyolefin articles. These stabilizer compositions surprisingly have multiple effects that lead to improved articles and/or processes, which include: reduction of time required to reach optimal physical and/or mechanical properties; improved viscosity leading to improved flow of resin and quicker mold fill time; and improved color stabilization of material, including lower or no discoloration due to yellowing.

Accordingly, in one aspect the invention provides stabilizer compositions having a stabilizing amount of a chroman-based compound according to Formula (V):

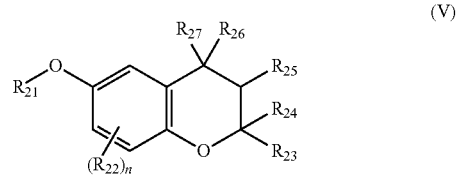

wherein $R_{21}$ is chosen from $COR_{28}$ or $Si(R_{29})_3$, wherein $R_{28}$ is chosen from H or a $C_1$-$C_{20}$ hydrocarbyl; and $R_{29}$ is chosen from a $C_1$-$C_{12}$ hydrocarbyl or alkoxy;

$R_{22}$ is a substituent that can be the same or different at from n=0 to 3 positions of the aromatic portion of Formula V and is independently chosen from H or a $C_1$-$C_{12}$ hydrocarbyl;

$R_{23}$ is chosen from H or a $C_1$-$C_{12}$ hydrocarbyl;

$R_{24}$ is chosen from H or a $C_1$-$C_{20}$ hydrocarbyl; and each of $R_{25}$-$R_{27}$ is independently chosen from a member selected from the group consisting of H; a $C_1$-$C_{12}$ hydrocarbyl; and $OR_{30}$, wherein $R_{30}$ is chosen from H or a $C_1$-$C_{12}$ hydrocarbyl; and $R_{27}$ is H, or a bond which together with $R_{26}$ forms =O.

In certain embodiments, the stabilizer composition can optionally include additional stabilizers chosen from, but not limited to, organic phosphites/phosphonites; hindered phenols; light stabilizers; and other chroman type compounds such as vitamin E or any of its isomers or mixtures of isomers, as well as certain modifiers such as, but not limited to, co-additives, nucleating agents, fillers, reinforcing agents, and polymer additives.

In another aspect, the invention provides processes for stabilizing an organic material subject to degradation and/or discoloration due to effects from light, oxygen, and/or heat, by adding a stabilizing amount of a stabilizer composition having a chroman-based compound according to Formula (V) as described above and hereinbelow.

In certain embodiments, the organic material can be a polyolefin type polymer or copolymer, an organic dye, wax, or ink.

Yet a further aspect of the invention provides methods for enhancing the processing stability of an organic material by admixing therein before or during processing a stabilizing amount of the stabilizer composition having a chroman-based compound according to Formula (V) as described above and hereinbelow.

In another aspect, the invention provides methods for reducing or preventing discoloration of an organic material by admixing therein before or during processing an effective amount of the stabilizer composition having a chroman-based compound according to Formula (V) as described above and hereinbelow.

In yet a further aspect, the invention provides masterbatch compositions having a stabilizer composition having a chroman-based compound according to Formula (V) as described above and hereinbelow, and an organic material that is identical to or compatible with the organic material to be stabilized.

The compositions and processes described herein are also useful for producing polymeric articles such as by any of the art recognized industrial molding processes including, for example, rotomolding, injection molding, blow molding, reel-to-reel molding, compression molding, micro molding, metal injection molding, etc., as well as for reducing cycle times and/or maintaining broad process windows in rotational molding processes for producing polymeric hollow articles.

Accordingly, in another aspect the invention provides processes for producing a molded article by adding a polymeric organic material and a polymer-stabilizing amount of a stabilizer composition having a chroman-based compound according to Formula (V) as described above and hereinbelow to a molding device or industrial molding process, and cycling the stabilized polymeric organic material through the device and/or process.

These and other objects, features and advantages of this invention will become apparent from the following detailed description of the various aspects of the invention taken in conjunction with the accompanying Figures and Examples.

BRIEF DESCRIPTION OF THE DRAWINGS

FIG. 1A—(A): polypropylene resin multi-pass extruded without stabilizer additive; (B): polypropylene resin multi-pass extruded with 0.15% of a stabilizer composition according to the invention (vitamin E acetate). FIG. 1B—(A): polypropylene resin multi-pass extruded without stabilizing additive; (B): polypropylene resin multi-pass extruded with 0.15% of vitamin E acetate; (C): polypropylene resin multi-pass extruded with 0.15% of vitamin E; (D): polypropylene resin multi-pass extruded with 0.075% each of vitamin E and vitamin E acetate. Example 1 below provides further information as to the experimental details and results.

DETAILED DESCRIPTION OF CERTAIN EMBODIMENTS OF THE INVENTION

Figure 1A:
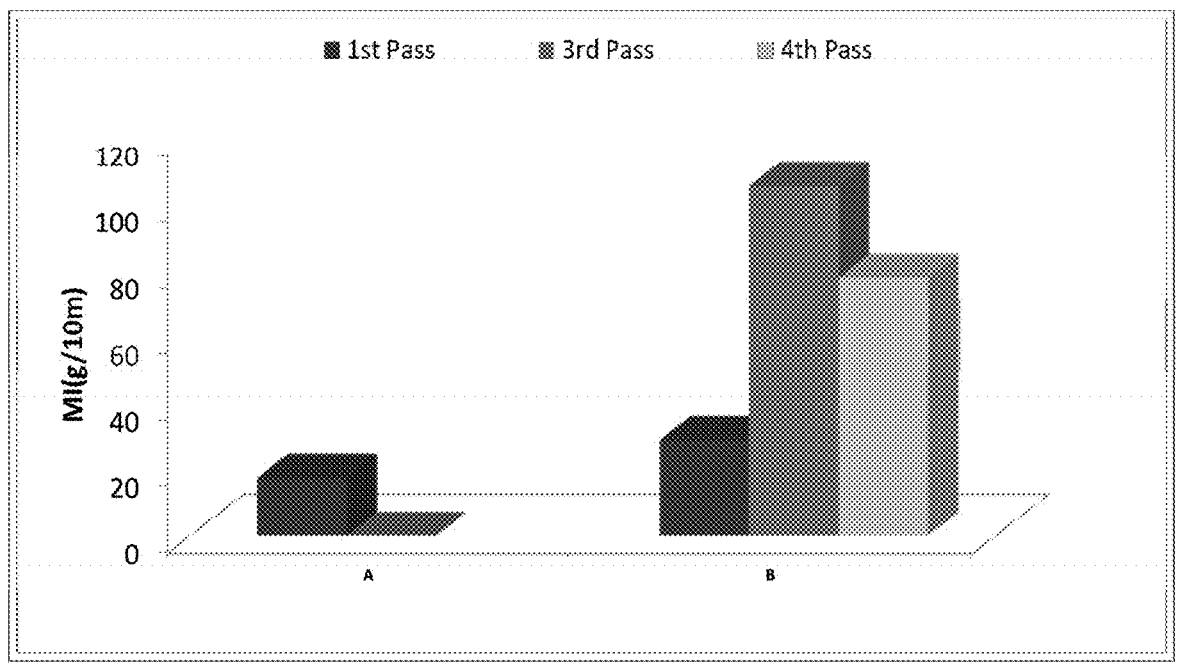
FIGS. 1A-B illustrate the Melt-Index results of polypropylene resin formulated with or without various stabilizer compositions, including those according to the present invention, and multi-pass extruded.

As employed above and throughout the disclosure, the following terms are provided to assist the reader. Unless otherwise defined, all terms of art, notations and other scientific terminology used herein are intended to have the meanings commonly understood by those of skill in the chemical arts. As used herein and in the appended claims, the singular forms include plural referents unless the context clearly dictates otherwise.

Throughout this specification the terms and substituents retain their definitions. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

The term "hydrocarbyl" is a generic term encompassing aliphatic, alicyclic and aromatic groups having an all-carbon backbone and consisting of carbon and hydrogen atoms. In certain cases, as defined herein, one or more of the carbon atoms making up the carbon backbone may be replaced or interrupted by a specified atom or group of atoms, such as by one or more heteroatom of N, O, and/or S. Examples of hydrocarbyl groups include alkyl, cycloalkyl, cycloalkenyl, carbocyclic aryl, alkenyl, alkynyl, alkylcycloalkyl, cycloalkylalkyl, cycloalkenylalkyl, and carbocyclic aralkyl, alkaryl, aralkenyl and aralkynyl groups. Such hydrocarbyl groups can also be optionally substituted by one or more substituents as defined herein. Accordingly, the chemical groups or moieties discussed in the specification and claims should be understood to include the substituted or unsubstituted forms. The examples and preferences expressed below also apply to each of the hydrocarbyl substituent groups or hydrocarbyl-containing substituent groups referred to in the various definitions of substituents for compounds of the formulas described herein unless the context indicates otherwise.

Preferred non-aromatic hydrocarbyl groups are saturated groups such as alkyl and cycloalkyl groups. Generally, and by way of example, the hydrocarbyl groups can have up to fifty carbon atoms, unless the context requires otherwise. Hydrocarbyl groups with from 1 to 30 carbon atoms are preferred. Within the sub-set of hydrocarbyl groups having 1 to 30 carbon atoms, particular examples are $C_{1-20}$ hydrocarbyl groups, such as $C_{1-12}$ hydrocarbyl groups (e.g. $C_{1-6}$ hydrocarbyl groups or $C_{1-4}$ hydrocarbyl groups), specific examples being any individual value or combination of values selected from $C_1$ through $C_{30}$ hydrocarbyl groups.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{30}$ or below.

Alkoxy or alkoxyalkyl refers to groups of from 1 to 20 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like.

Acyl refers to formyl and to groups of 1, 2, 3, 4, 5, 6, 7, 8, 9, 10, 11 and 12 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl, t-butoxycarbonyl, benzyloxycarbonyl and the like. Lower-acyl refers to groups containing one to six carbons.

References to "carbocyclic" or "cycloalkyl" groups as used herein shall, unless the context indicates otherwise, include both aromatic and non-aromatic ring systems. Thus, for example, the term includes within its scope aromatic, non-aromatic, unsaturated, partially saturated and fully saturated carbocyclic ring systems. In general, such groups may be monocyclic or bicyclic and may contain, for example, 3 to 12 ring members, more usually 5 to 10 ring members. Examples of monocyclic groups are groups containing 3, 4, 5, 6, 7, and 8 ring members, more usually 3 to 7, and preferably 5 or 6 ring members. Examples of bicyclic groups are those containing 8, 9, 10, 11 and 12 ring members, and more usually 9 or 10 ring members. Examples of non-aromatic carbocycle/cycloalkyl groups include c-propyl, c-butyl, c-pentyl, c-hexyl, and the like. Examples of $C_7$ to $C_{10}$ polycyclic hydrocarbons include ring systems such as norbornyl and adamantyl.

Aryl (carbocyclic aryl) refers to a 5- or 6-membered aromatic carbocyclic ring containing; a bicyclic 9- or 10-membered aromatic ring system; or a tricyclic 13- or 14-membered aromatic ring system. The aromatic 6- to 14-membered carbocyclic rings include, e.g., substituted or unsubstituted phenyl groups, benzene, naphthalene, indane, tetralin, and fluorene.

Substituted hydrocarbyl, alkyl, aryl, cycloalkyl, alkoxy, etc. refer to the specific substituent wherein up to three H atoms in each residue are replaced with alkyl, halogen, haloalkyl, hydroxy, alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, halobenzyl, heteroaryl, phenoxy, benzyloxy, heteroaryloxy, benzoyl, halobenzoyl, or loweralkylhydroxy.

The term "halogen" means fluorine, chlorine, bromine or iodine.

As used herein, the term "chroman" or "chroman-based compound" refers to those compounds having a functional chroman group as part of the compound. In certain embodiments the chroman-based compound will be substituted. In other embodiments, the chroman-based compound can include chromanones. Coumarin, tocopherols, and tocotrienols are specific examples of chroman-based compounds.

The terms "cycle time" or "molding cycle" as used herein are given their ordinary meaning as commonly understood by those of skill in the industrial molding arts and refer to the time from one point in the molding cycle to the corresponding point in the next repeated sequence (i.e., the time required to produce a part in a molding operation as measured from a point of one operation to the same point of the first repeat of the operation).

The terms "optimal mechanical property" or "optimal physical property" as used herein refer to molded parts having the most desirable: impact strength, coalescence or scintering of polymer particles, and general appearance such as color.

The term "organic material" or "material to be stabilized" as used herein refers to nonliving organic material including, for example, cosmetic preparations such as ointments and lotions, drug formulations such as pills and suppositories, photographic recording materials, organic dyes, inks, and fibers, as well as synthetic and natural organic polymers, and biopolymers. The synthetic organic polymers are exemplified by synthetic resin such as thermoplastic resin, thermosetting resin and the like. Various such resins are known to those of ordinary skill in the art and are suitable for use with the present invention. The natural organic polymers are exemplified by natural rubbers, proteins, cellulosic derivatives, mineral oils, animal or vegetable oils, wax, fats and oils and the like.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The stabilizer compositions according to the invention and suitable for use in stabilizing organic materials subject to degradation and/or discoloration due to the effects from light, oxygen and heat, and in processes for producing articles from organic materials blended therewith, include at least one chroman-based compound according to Formula V:

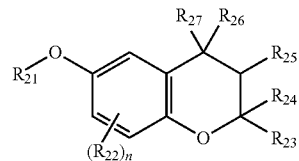
(V)

wherein $R_{21}$ is chosen from $COR_{28}$ or $Si(R_{29})_3$, wherein $R_{28}$ is chosen from H or a $C_1$-$C_{20}$ hydrocarbyl; and $R_{29}$ is chosen from a $C_1$-$C_{12}$ hydrocarbyl or alkoxy;

$R_{22}$ is a substituent that can be the same or different at from n=0 to 3 positions of the aromatic portion of Formula V and is independently chosen from H or a $C_1$-$C_{12}$ hydrocarbyl;

$R_{23}$ is chosen from H or a $C_1$-$C_{12}$ hydrocarbyl;

$R_{24}$ is chosen from H or a $C_1$-$C_{20}$ hydrocarbyl; and each of $R_{25}$-$R_{27}$ is independently chosen from a member selected from the group consisting of H; a $C_1$-$C_{12}$ hydrocarbyl; and $OR_{30}$, wherein $R_{30}$ is chosen from H or a $C_1$-$C_{12}$ hydrocarbyl; and $R_{27}$ is H, or a bond which together with $R_{26}$ forms =O.

In certain embodiments, $R_{24}$ is a $C_1$-$C_{18}$ hydrocarbyl.

In some embodiments, the chroman-based compound is vitamin E acetate according to Formula (Va)

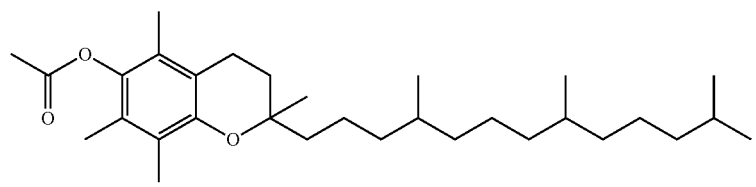
(Va)

or isomers and/or mixtures thereof, including mixtures of isomers.

In certain embodiments, the stabilizer composition includes two or more chroman-based compounds according to Formula (V), or a chroman-based compound according to Formula (V) and another chroman compound. In certain embodiments, the other chroman compound is a tocopherol or tocotrienol.

The chroman-based compound can be present from 0.001 to 5.0% by weight of the total weight of the stabilizer composition, preferably from 0.01 to 2.0% by weight of the total weight of the stabilizer composition, and more preferably from 0.01 to 1.0% by weight of the total weight of the stabilizer composition. In certain embodiments, the chroman-based compound is present at 0.05% by weight of the total weight of the stabilizer composition.

In certain embodiments, the stabilizer composition can further include at least one compound chosen from the group of organic phosphites or phosphonites. In some embodiments the organic phosphite or phosphonite compound includes at least one organic phosphite or phosphonite chosen from a compound according to Formulas 1-7:

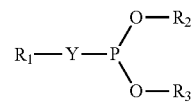
(1)

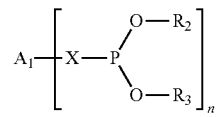
(2)

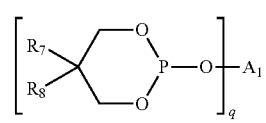
(3)

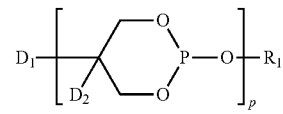
(4)

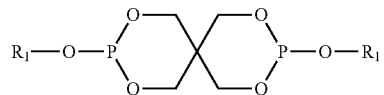
(5)

-continued

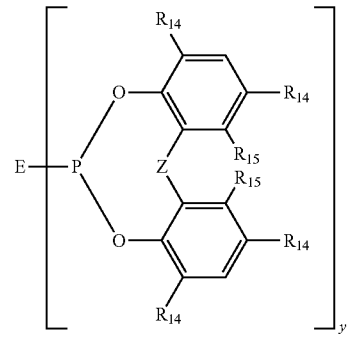
(6)

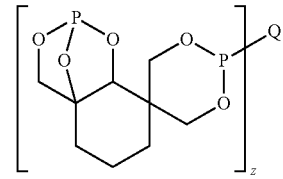
(7)

in which the indices are integral and
n is 2, 3 or 4; p is 1 or 2; q is 2 or 3; r is 4 to 12; y is 1, 2 or 3; and z is 1 to 6;
$A_1$, if n is 2, is $C_2$-$C_{18}$ alkylene; $C_2$-$C_{12}$ alkylene interrupted by oxygen, sulfur or —$NR_4$—; a radical of the formula

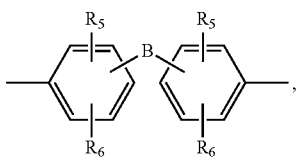

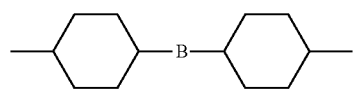

or phenylene;
$A_1$, if n is 3, is a radical of the formula —$C_rH_{2r-1}$—;
$A_1$, if n is 4, is

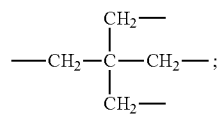

$A_2$ is as defined for $A_1$ if n is 2;
B is a direct bond, —$CH_2$—, —$CHR_4$—, —$CR_1R_4$—, sulfur, $C_5$-$C_7$ cycloalkylidene, or cyclohexylidene which is substituted by from 1 to 4 $C_1$-$C_4$ alkyl radicals in position 3, 4 and/or 5;
$D_1$, if p is 1, is $C_1$-$C_4$ alkyl and, if p is 2, is —$CH_2OCH_2$—;
$D_2$, if p is 1, is $C_1$-$C_4$ alkyl;
E, if y is 1, is $C_1$-$C_{18}$ alkyl, —$OR_1$ or halogen;
E, if y is 2, is —O-$A_2$-O—,
E, if y is 3, is a radical of the formula $R_4C(CH_2O—)_3$ or $N(CH_2CH_2O—)_3$;
Q is the radical of an at least z-valent alcohol or phenol, this radical being attached via the oxygen atom to the phosphorus atom;
$R_1$, $R_2$ and $R_3$ independently of one another are $C_1$-$C_{18}$ alkyl which is unsubstituted or substituted by halogen, —$COOR_4$, —CN or —$CONR_4R_4$; $C_2$-$C_{18}$ alkyl interrupted by oxygen, sulfur or —$NR_4$—; $C_7$-$C_9$ phenylalkyl; $C_5$-$C_{12}$ cycloalkyl, phenyl or naphthyl; naphthyl or phenyl substituted by halogen, 1 to 3 alkyl radicals or alkoxy radicals having a total of 1 to 18 carbon atoms or by $C_7$-$C_9$ phenylalkyl; or a radical of the formula

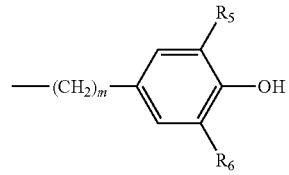

in which m is an integer from the range 3 to 6;
$R_4$ is hydrogen, $C_1$-$C_8$ alkyl, $C_5$-$C_{12}$ cycloalkyl or $C_7$-$C_9$ phenylalkyl,
$R_5$ and $R_6$ independently of one another are hydrogen, $C_1$-$C_8$ alkyl or $C_5$-$C_6$ cycloalkyl,
$R_7$ and $R_8$, if q is 2, independently of one another are $C_1$-$C_4$ alkyl or together are a 2,3-dehydropentamethylene radical; and
$R_7$ and $R_8$, if q is 3, are methyl;
$R_{14}$ is hydrogen, $C_1$-$C_9$ alkyl or cyclohexyl,
$R_{15}$ is hydrogen or methyl and, if two or more radicals $R_{14}$ and $R_{15}$ are present, these radicals are identical or different,
X and Y are each a direct bond or oxygen,
Z is a direct bond, methylene, —$C(R_{16})_2$— or sulfur, and
$R_{16}$ is $C_1$-$C_8$ alkyl;
a trisarylphosphite according to Formula 8:

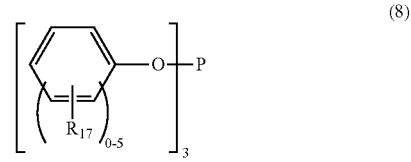

wherein $R_{17}$ is a substituent that is the same or different at from 0 to 5 positions of the aromatic portion of Formula 8 and is independently chosen from $C_1$-$C_{20}$ alkyl, $C_3$-$C_{20}$ cycloalkyl, $C_4$-$C_{20}$ alkyl cycloalkyl, $C_6$-$C_{10}$ aryl, and $C_7$-$C_{20}$ alkylaryl; and combinations thereof.

In some embodiments, the following organic phosphites or phosphonites are preferred: triphenyl phosphite; diphenyl alkyl phosphites; phenyl dialkyl phosphites; trilauryl phosphite; trioctadecyl phosphite; distearyl pentaerythritol phosphite; tris(2,4-di-tert-butylphenyl)phosphite; tris(nonylphenyl)phosphite; a compound of formulae (A), (B), (C), (D), (E), (F), (G), (H), (J), (K) and (L):

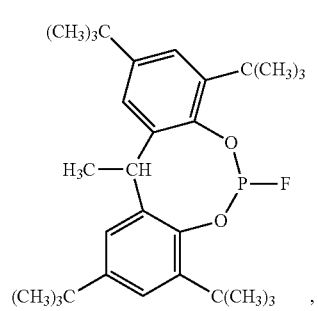
(A)

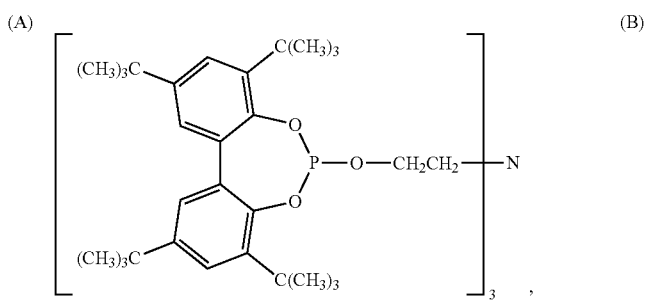
(B)

-continued
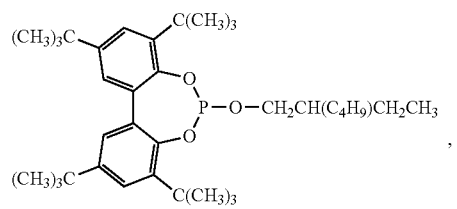 (C)
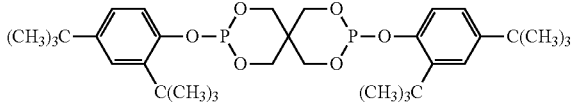 (D)
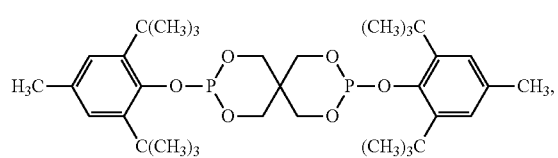 (E)
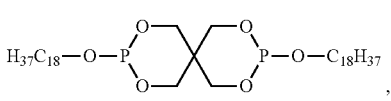 (F)
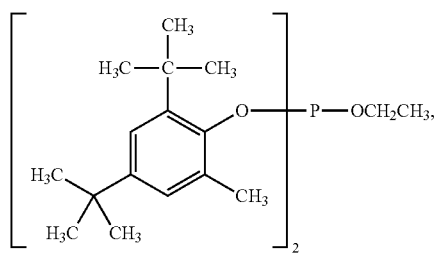 (G)
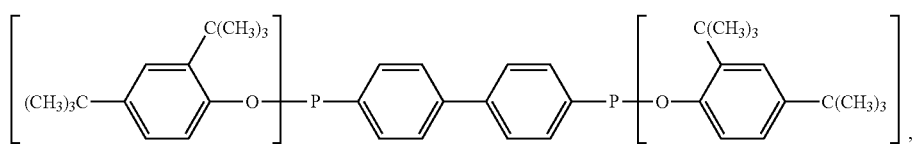 (H)
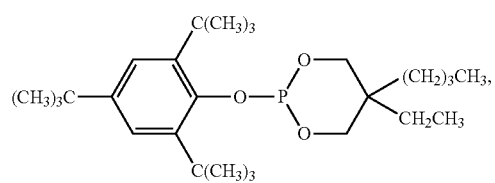 (J)
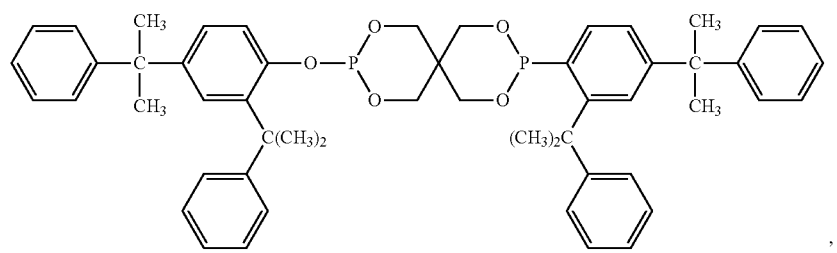 (K)
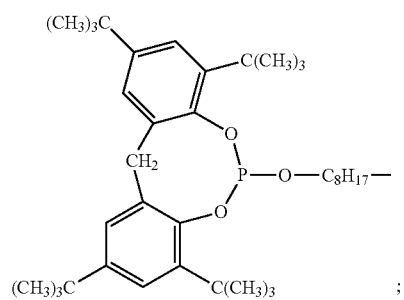 (L)
2-butyl-2-ethyl-1,3-propanediol 2,4,6-tri-t-butylphenol phosphite; bis-(2,6-di-t-butyl-4-methlphenyl)pentaerythritol diphosphite; 2-butyl-2-ethyl-1,3-propanediol 2,4-di-cumylphenol phosphite; 2-butyl-2-ethyl-1,3-propanediol 4-methyl-2,6-di-t-butylphenol phosphite; and bis-(2,4,6-tri-t-butyl-phenyl)pentaerythritol diphosphite.

The following organic phosphites and phosphonites are particularly suitable for use in the rotomolding processes described herein: tris(2,4-di-tert-butylphenyl)phosphite (IR-GAFOS® 168); Bis(2,4-dicumylphenyl)pentaerythritol diphosphite (DOVERPHOS® S9228); and tetrakis(2,4-di-tert-butylphenyl)4,4'-biphenylene-diphosphonite (IR-GAFOS® P-EPQ).

The organic phosphites or phosphonites can be present in an amount from 0.01% to 10% by weight based on the total weight of the organic material to be stabilized. Preferably, the amount of organic phosphite or phosphonite is available from 0.05 to 5%, and more preferably from 0.1 to 3% by weight based on the total weight of the organic material to be stabilized.

In certain embodiments, the stabilizer composition can further include at least one hindered phenol compound. Suitable hindered phenols for use with the rotomolding processes described herein include, but are not limited to, those having a molecular fragment according to one or more of Formula (IVa), (IVb), or (IVc):

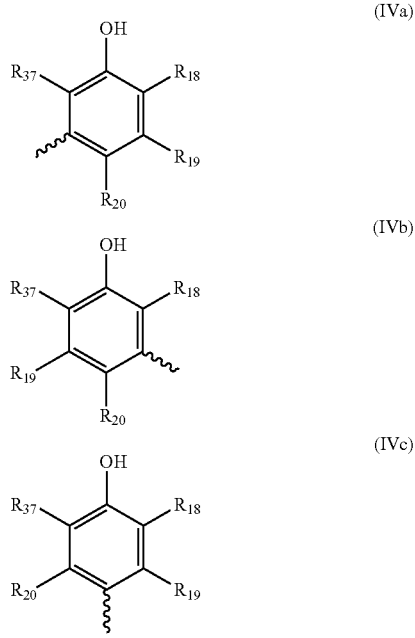

wherein

"⁓"

indicates the point of attachment (via a carbon bond) of the molecular fragment to a parent compound, and wherein $R_{18}$ is chosen from hydrogen and a $C_{1-4}$ hydrocarbyl; $R_{19}$ and $R_{20}$ are the same or different and are independently chosen from hydrogen and a $C_1$-$C_{20}$ hydrocarbyl; and $R_{37}$ is chosen from a $C_1$-$C_{12}$ hydrocarbyl. In some embodiments, $R_{18}$ and $R_{37}$ are independently chosen from methyl and t-butyl.

The following compounds exemplify some hindered phenols that are suitable for use in the compositions and processes of the invention: (1,3,5-Tris(4-t-butyl-3-hydroxy-2,6-dimethylbenzyl)-1,3,5-triazine-2,4,6-(1H,3H,5H)-trione; 1,3,5-tris(3,5-di-tert-butyl-4-hydroxybenzyl)-1,3,5-triazine-2,4,6(1H,3H,5H)-trione (IRGANOX® 3114); 1,1,3-Tris(2'-methyl-4'-hydroxy-5'-t-butylphenyl)butane; Triethylene glycol bis[3-(3-t-butyl-4-hydroxy-5-methylphenyl)propionate]; 4,4'-Thiobis(2-t-butyl-5-methylphenol); 2,2'-Thiodiethylene bis[3-(3-t-butyl-4-hydroxyl-5-methylphenyl)propionate]; Octadecyl 3-(3'-t-butyl-4'-hydroxy-5'-methylphenyl)propionate; Tetrakismethylene(3-t-butyl-4-hydroxy-5-methylhydrocinnamate)methane; N,N'-Hexamethylene bis[3-(3-t-butyl-4-hydroxy-5-methylphenyl)propionamide]; Di(4-tertiarybutyl-3-hydroxy-2,6-dimethyl benzyl)thiodipropionate; and octadecyl 3,5-di-(tert)-butyl-4-hydroxyhydrocinnamate.

Other phenols also suitable for use with processes and compositions of the invention are known to those of skill in the art and include, for example:

2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4 isobutylphenol; 2,6-dicyclopentyl-4-methylphenol; 2-(α-methylcyclohexyl)-4,6 dimethylphenol; 2,6-di-octadecyl-4-methylphenol; 2,4,6,-tricyclohexyphenol; and 2,6-di-tert-butyl-4-methoxymethylphenol;

2,2'-methylene-bis-(6-tert-butyl-4-methylphenol) (CYANOX® 2246); 2,2'-methylene-bis-(6-tert-butyl-4-ethylphenol) (CYANOX® 425); 2,2'-methylene-bis-(4-methyl-6-(α-methylcyclohexyl)phenol); 2,2'-methylene-bis-(4-methyl-6-cyclohexylphenol); 2,2'-methylene-bis-(6-nonyl-4-methylphenol); 2,2'-methylene-bis-(6-nonyl-4methylphenol); 2,2'-methylene-bis-(6-(α-methylbenzyl)-4-nonylphenol); 2,2'-methylene-bis-(6-(α,α-dimethylbenzyl)-4-nonyl-phenol); 2,2'-methylene-bis-(4,6-di-tert-butylphenol); 2,2'-ethylidene-bis-(6-tert-butyl-4-isobutylphenol); 4,4'methylene-bis-(2,6-di-tert-butylphenol); 4,4'-methylene-bis-(6-tert-butyl-2-methylphenol); 1,1-bis-(5-tert-butyl-4-hydroxy-2-methylphenol)butane 2,6-di-(3-tert-butyl-5-methyl-2-hydroxybenzyl)-4-methylphenol; 1,1,3-tris-(5-tert-butyl-4-hydroxy-2-methylphenyl)butane; 1,1-bis-(5-tert-butyl-4-hydroxy2 methylphenyl)-3-dodecyl-mercaptobutane; ethyleneglycol-bis-(3,3,-bis-(3'-tert-butyl-4'-hydroxyphenyl)-butyrate)-di-(3-tert-butyl-4-hydroxy-5-methylpenyl)-dicyclopentadiene; di-(2-(3'-tert-butyl-2'hydroxy-5'methylbenzyl)-6-tert-butyl-4-methylpheny-1)terephthalate; and other phenolics such as monoacrylate esters of bisphenols such as ethylidiene bis-2,4-di-t-butylphenol monoacrylate ester;

Hydroquinones such as 2,6-di-tert-butyl-4-methoxyphenol; 2,5-di-tert-butylhydroquinone; 2,5-di-tert-amyl-hydroquinone; and 2,6-diphenyl-4-octadecyloxyphenol; and Thiodiphenyl ethers such as 2,2'-thio-bis-(6-tert-butyl-4-methylphenol); 2,2'-thio-bis-(4-octylphenol); 4,4'thio-bis-(6-tert-butyl-3-methylphenol); and 4,4'-thio-bis-(6-tert-butyl-2-methylphenol).

The stabilizer compositions according to the invention may further include one or more co-stabilizers and/or additives that include, but are not limited to: hindered amine light stabilizers, hindered hydroxyl benzoates, nickel phenolates, ultraviolet light stabilizers, antioxidants, and combinations thereof in an amount effective to stabilize the organic material against the degradative effects of visible and/or ultraviolet light radiation.

Suitable hindered amine light stabilizers for use with the processes and stabilizer compositions according to the invention include, for example, compounds having a molecular fragment according to Formula (VI):

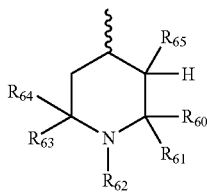

(VI)

wherein $R_{62}$ is chosen from a member selected from the group consisting of hydrogen; OH; $C_1$-$C_{20}$ hydrocarbyl; —$CH_2CN$; $C_1$-$C_{12}$ acyl; and $C_1$-$C_{18}$ alkoxy;

$R_{65}$ is chosen from a member selected from the group consisting of hydrogen; and $C_1$-$C_8$ hydrocarbyl; and each of $R_{60}$, $R_{61}$, $R_{63}$, and $R_{64}$ is independently chosen from a $C_1$-$C_{20}$ hydrocarbyl, or $R_{60}$ and $R_{61}$ and/or $R_{63}$ and $R_{64}$ taken together with the carbon to which they are attached form a $C_5$-$C_{10}$ cycloalkyl;

or Formula (VIa)

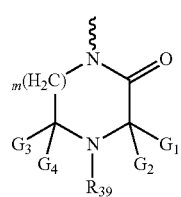

(VIa)

wherein m is an integer from 1 to 2;

$R_{39}$ is chosen from: hydrogen; OH; $C_1$-$C_{20}$ hydrocarbyl; —$CH_2CN$; $C_1$-$C_{12}$ acyl; and $C_1$-$C_{18}$ alkoxy; and each of $G_1$-$G_4$ is independently chosen from $C_1$-$C_{20}$ hydrocarbyl.

Hindered amine light stabilizers particularly suitable for use with the present invention include, but are not limited to, bis(2,2,6,6-tetramethylpiperidin-4-yl)sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl)n-butyl 3,5-di-tert-butyl-4-hydroxybenzylmalonate; a condensate of 1-(2-hydroxyethyl)-2,2,6,6-tetramethyl-4-hydroxypiperidine and succinic acid; 2,2,6,6-tetramethylpiperidin-4-yl stearate; 2,2,6,6-tetramethylpiperidin-4-yl dodecanate; 1,2,2,6,6-pentamethylpiperidin-4-yl stearate; 1,2,2,6,6-pentamethylpiperidin-4-yl dodecanate; a condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl)nitrilotriacetate; tetrakis(2,2,6,6-tetramethylpiperidin-4-yl)-1,2,3,4-butanetetracarboxylate; 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; a condensate of N,N'-bis(2,2,6,6-tetramethylpiperidin-4-yl)hexamethylenediamine and 4-morpholino-2,6-dichloro-1,3,5-triazine; a condensate of 2 chloro-4,6-bis(4-n-butylamino-2,2,6,6-tetramethylpiperidyl)-1,3,5-triazine and 1,2-bis(3-aminopropylamino)ethane; a condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; a condensate of N,N'-bis(2,2,6,6-tetramethylpiperidin-4-yl)hexamethylenediamine and 4-cyclohexylamino-2,6-dichloro-1,3,5-triazine; a condensate of 1,2-bis(3-aminopropylamino)ethane, 2,4,6-trichloro-1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines; a reaction product of 7,7,9,9-tetramethyl-2-cycloundecyl-1-oxa-3,8-diaza-4-oxospiro [4.5]decane and epichlorohydrin;

N-alkoxy hindered amine light stabilizers including, but not limited to, tetrakis(2,2,6,6-tetramethyl-4-piperidyl)butane-1,2,3,4-tetracarboxylate (MARK® LA-57); 1,2,3,4-butanetetracarboxylic acid, tetrakis(1,2,2,6,6-pentamethyl-4-piperidinyl)ester (MARK® LA-52); 1,2,3,4-butanetetracarboxylic acid, 1,2,2,6,6-pentamethyl-4-piperidinyl tridecyl ester (MARK® LA-62); 1,2,3,4-butanetetracarboxylic acid, 2,2,6,6-tetramethyl-4-piperidinyl tridecyl ester (MARK® LA-67); 1,2,3,4-butanetetracarboxylic acid, polymer with 2,2,6,6-tetramethyl-2,4,8,10-tetraoxaspiro[5.5]-undecane-3,9-diethanol,1,2,2,6,6-pentamethyl-4-piperidinyl ester (MARK® LA-63); 1,2,3,4-butanetetracarboxylic acid, polymer with 2,2,6,6-tetramethyl-2,4,8,10-tetraoxaspiro[5.5]-undecane-3,9-diethanol, 2,2,6,6-tetramethyl-4-piperidinyl ester (MARK® LA-68); bis(1-undecanoxy-2,2,6,6-tetramethylpiperidin-4-yl)carbonate (MARK® LA-81; aka STAB® LA-81 available from Adeka Palmarole, Saint-Louis, France); TINUVIN® 123; TINUVIN® NOR 371; TINUVIN® XT-850/XT-855; FLAMESTAB® NOR 116; and those disclosed in EP 0 889 085;

hydroxyl-substituted N-alkoxy HALS including, but not limited to, those disclosed in U.S. Pat. No. 6,271,377 such as 1-(2-hydroxy-2-methylpropoxy)-2,2,6,6-tetramethyl-4-piperidinol; 1-(2-hydroxy-2-methylpropoxy)-4-octadecanoyloxy-2,2,6,6-tetramethylpiperidine; 1-(4-octadecanoyloxy-2,2,6,6-tetramethylpiperidin-1-yloxy)-2-octadecanoyloxy-2-methylpropane; 1-(2-hydroxyethyl)-2,2,6,6-tetramethyl-4-piperidinol; a reaction product of 1-(2-hydroxyethyl)-2,2,6,6-tetramethyl-4-piperidinol and dimethylsuccinate;

any of the tetramethylpiperidyl groups disclosed in WO 2007/104689 including, but not limited to, 2,2,4,4-tetramethyl-7-oxa-3,20-diazadispiro[5.1.11.2]heneicosan-21-one (HOSTAVIN® N20); the ester of 2,2,6,6-tetramethyl-4-piperidinol with higher fatty acids (CYASORB® 3853); 3-dodecyl-1-(2,2,6,6-tetramethyl-4-piperidyl)pyrrolidine-2,5-dione (SANDUVOR® 3055); and their wax reaction products such as HALS NOW (LS X—N—O—W1);

piperizinone compounds and derivatives thereof disclosed in U.S. Pat. Nos. 6,843,939; 7,109,259; 4,240,961; 4,480,092; 4,629,752; 4,639,479; 5,013,836; 5,310,771; and WO 88/08863 including, but not limited to, 1H-Pyrrole-2,5-dione, 1-octadecyl-, polymer with (1-methylethenyl)benzene and 1-(2,2,6,6-tetramethyl-4-piperidinyl)-1H-pyrrole-2,5-dione; piperazinone, 1,1',1''-[1,3,5-triazine-2,4,6-triyltris[(cyclohexylimino)-2,1-ethanediyl]]tris[3,3,5,5-tetramethyl-; piperazinone, 1,1',1''-[1,3,5-triazine-2,4,6-triyltris[(cyclohexylimino)-2,1-ethanediyl]]tris[3,3,4,5,5- pentamethyl-; the reaction product of 7,7,9,9-tetramethyl-2-cycloundecyl-1-oxa-3,8-diaza-4-oxospiro[4.5]decane and epichlorohydrin; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 2-[(2-hydroxyethyl)amino]-4,6-bis[N-(1-cyclohexyloxy-2,2,6,6-tetramethylpiperidin-4-yl)butylamino-1,3,5-triazine; propanedioic acid, [(4-methoxyphenyl)-methylene]-bis-(1,2,2,6,6-pentamethyl-4-piperidinyl)ester; tetrakis(2,2,6,6-tetramethylpiperidin-4-yl)-1,2,3,4-butanetetracarboxylate; benzenepropanoic acid, 3,5-bis(1,1-dimethylethyl)-4-hydroxy-, 1-[2-[3-[3,5-bis(1,1-dimethylethyl)-4-hydroxyphenyl]-1-oxopropoxy]ethyl]-2,2,6,6-tetramethyl-4-piperidinyl ester; N-(1-octyloxy-2,2,6,6-tetramethylpiperidin-4-yl)-N'-dodecyloxalamide; tris(2,2,6,6-tetramethylpiperidin-4-yl)nitrilotriacetate; 1,5-dioxaspiro{5,5}undecane-3,3-dicarboxylic acid, bis(1,2,2,6,6-pentamethyl-4-piperidinyl): 1,5-dioxaspiro{5,5}undecane-3,3-dicarboxylic acid, bis(2,2,6,6-tetramethyl-4-piperidinyl); the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; 1,2,3,4-butanetetracarboxylic acid, 1,2,2,6,6-pentamethyl-4-piperidinyl tridecyl ester; tetrakis(2,2,6,6-tetramethylpiperidin-4-yl)-1,2,3,4-butanetetracarboxylate; 1,2,3,4-butanetetracarboxylic acid, 2,2,6,6-tetramethyl-4-piperidinyl tridecyl ester; tetrakis(1,2,2,6,6-pentamethylpiperidin-4-yl)-1,2,3,4-butanetetracarboxylate; mixture of 2,2,4,4-tetramethyl-21-oxo-7-oxa-3.20-diazaspiro(5.1.11.2)-heneicosane-20-propanoic acid-dodecylester and 2,2,4,4-tetramethyl-21-oxo-7-oxa-3.20-diazaspiro(5.1.11.2)-heneicosane-20-propanoic acid-tetradecylester; 1H,4H,5H,8H-2,3a,4a,6,7a,8a-hexaazacyclopenta[def]fluorene-4,8-dione, hexahydro-2,6-bis(2,2,6,6-tetramethyl-4-piperidinyl)-; polymethyl[propyl-3-oxy(2',2',6',6'-tetramethyl-4,4'-piperidinyl)]siloxane; polymethyl[propyl-3-oxy(1',2',2',6',6'-pentamethyl-4,4'-piperidinyl)]siloxane; copolymer of methylmethacrylate with ethyl acrylate and 2,2,6,6-tetramethylpiperidin-4-yl acrylate; copolymer of mixed $C_{20}$ to $C_{24}$ alpha-olefins and (2,2,6,6-tetramethylpiperidin-4-yl)succinimide; 1,2,3,4-butanetetracarboxylic acid, polymer with β,β,β',β'-tetramethyl-2,4,8,10-tetraoxaspiro[5.5]undecane-3,9-diethanol, 1,2,2,6,6-pentamethyl-4-piperidinyl ester; 1,2,3,4-butanetetracarboxylic acid, polymer with β,β,β',β'-tetramethyl-2,4,8,10-tetraoxaspiro[5.5]undecane-3,9-diethanol, 2,2,6,6-tetramethyl-4-piperidinyl ester copolymer; 1,3-benzenedicarboxamide, N,N'-bis(2,2,6,6-tetramethyl-4-piperidinyl; 1,1'-(1,10-dioxo-1,10-decanediyl)-bis(hexahydro-2,2,4,4,6-pentamethylpyrimidine; ethane diamide, N-(1-acetyl-2,2,6,6-tetramethylpiperidinyl)-N'-dodecyl; formamide, N,N'-1,6-hexanediylbis[N-(2,2,6,6-tetramethyl-4-piperidinyl); D-glucitol, 1,3:2,4-bis-O-(2,2,6,6-tetramethyl-4-piperidinylidene)-; 2,2,4,4-tetramethyl-7-oxa-3,20-diaza-21-oxo-dispiro[5.1.11.2]heneicosane; propanamide, 2-methyl-N-(2,2,6,6-tetramethyl-4-piperidinyl)-2-[(2,2,6,6-tetramethyl-4-piperidinyl)amino]-; 7-oxa-3,20-diazadispiro[5.1.11.2]heneicosane-20-propanoic acid, 2,2,4,4-tetramethyl-21-oxo-, dodecyl ester; N-(2,2,6,6-tetramethylpiperidin-4-yl)-β-aminopropionic acid dodecyl ester; N-(2,2,6,6-tetramethylpiperidin-4-yl)-N'-aminooxalamide; propanamide, N-(2,2,6,6-tetramethyl-4-piperidinyl)-3-[(2,2,6,6-tetramethyl-4-piperidinyl)amino]-; mixture of 4-hexadecyloxy- and 4-stearyloxy-2,2,6,6-tetramethylpiperidine; 3-dodecyl-1-(1,2,2,6,6-pentamethylpiperidin-4-yl) pyrrolidine-2,5-dione; 3-dodecyl-1-(1-ethanoyl-2,2,6,6-pentamethylpiperidin-4-yl)pyrrolidine-2,5-dione; bis(2,2,6,6-tetramethylpiperidin-4-yl)succinate; bis(1,2,2,6,6-pentamethylpiperidin-4-yl)n-butyl 3,5-di-tert-butyl-4-hydroxybenzylmalonate; tris(2,2,6,6-tetramethylpiperidin-4-yl)nitrilotriacetate; 1,1'-(1,2-ethanediyl)bis(3,3,5,5-tetramethylpiperazinone); 4-benzoyl-2,2,6,6-tetramethylpiperidine; 4-stearyloxy-2,2,6,6 tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; 2-undecyl-7,7,9,9-tetramethyl-1-oxa-3,8-diaza-4-oxospiro[4.5]decane; 1,5-dioxaspiro {5,5}undecane-3,3-dicarboxylic acid, bis(2,2,6,6-tetramethyl-4-piperidinyl) and 1,5-dioxaspiro{5,5}undecane-3,3-dicarboxylic acid, bis(1,2,2,6,6-pentamethyl-4-piperidinyl); $N^1$-(β-hydroxyethyl)3,3-pentamethylene-5,5-dimethylpiperazin-2-one; $N^1$-tert-octyl-3,3,5,5-tetramethyl-diazepin-2-one; $N^1$-tert-octyl-3,3-pentamethylene-5,5-hexamethylene-diazepin-2-one; $N^1$-tert-octyl-3,3-pentamethylene-5,5-dimethylpiperazin-2-one; trans-1,2-cyclohexane-bis-($N^1$-5,5-dimethyl-3,3-pentamethylene-2-piperazinone); trans-1,2-cyclohexane-bis-($N^1$-3,3,5,5-dispiropentamethylene-2-piperazinone); $N^1$-isopropyl-1,4-diazadispiro-(3,3,5,5)pentamethylene-2-piperazinone; $N^1$-isopropyl-1,4-diazadispiro-3,3-pentamethylene-5,5-tetramethylene-2-piperazinone; $N^1$-isopropyl-5,5-dimethyl-3,3-pentamethylene-2-piperazinone; trans-1,2-cyclohexane-bis-$N^1$-(dimethyl-3,3-pentamethylene-2-piperazinone); $N^1$-octyl-5,5-dimethyl-3,3-pentamethylene-1,4-diazepin-2-one; and $N^1$-octyl-1,4-diazadispiro-(3,3,5,5) pentamethylene-1,5-diazepin-2-one. Other sterically hindered amines suitable for use with the invention include, for example, any of those disclosed in EP 1 308 084.

The hindered amine component can be present in an amount from 0.01 to 10% by weight based on the total weight of the organic material to be stabilized. Preferably, the amount of hindered amine is available from 0.05 to 5%, and more preferably from 0.1 to 3% by weight based on the total weight of the organic material to be stabilized.

Other light stabilizers suitable for use with the present invention include one or more of the following:

2-(2'-Hydroxyphenyl)benzotriazoles, for example 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chloro-benzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)benzotriazole; 2-(2'-hydroxy-4'-octyloxyphenyl)benzotriazole; 2-(3',5'-di-tert-amyl-2'-hydroxyphenyl)benzotriazole; 2-(3',5'-bis- (α,α-dimethylbenzyl)-2'-hydroxyphenyl)benzotriazole; 2-(3'-tert-butyl-2'-hydroxy-5'-(2-octyloxycarbonylethyl) phenyl)-5-chloro-benzotriazole; 2-(3'-tert-butyl-5'-[2-(2-ethylhexyloxy)-carbonylethyl]-2'-hydroxyphenyl)-5-chloro-benzotriazole; 2-(3'-tert-butyl-2'-hydroxy-5'-(2-methoxycarbonylethyl)phenyl)-5-chloro-benzotriazole; 2-(3'-tert-butyl-2'-hydroxy-5'-(2-methoxycarbonylethyl) phenyl)benzotriazole; 2-(3'-tert-butyl-2'-hydroxy-5'-(2-octyloxycarbonylethyl)phenyl)benzotriazole; 2-(3'-tert-butyl-5'-[2-(2-ethylhexyloxy)carbonyl]-2'-hydroxyphenyl) benzotriazole; 2-(3'-dodecyl-2'-hydroxy-5'-methylphenyl) benzotriazole; 2-(3'-tert-butyl-2'-hydroxy-5'-(2-isooctyloxycarbonylethyl)phenylbenzotriazole; 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$]$_2$ where R=3'-tert-butyl-4'-hydroxy-5'-2H-benzotriazol-2-ylphenyl; 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl] benzotriazole;

2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives;

Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate;

Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands; and 2-(2'-hydroxyphenyl)-1,3,5-triazine compounds according to Formula (VII):

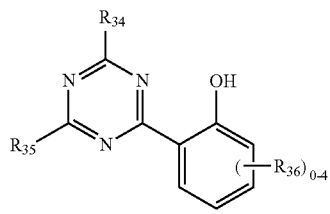

(VII)

wherein each of $R_{34}$ and $R_{35}$ is independently chosen from an optionally substituted $C_6$-$C_{10}$ aryl group, $C_1$-$C_{10}$ hydrocarbyl-substituted amino, $C_1$-$C_{10}$ acyl and $C_1$-$C_{10}$ alkoxyl; and wherein $R_{36}$ is a substituent that is the same or different at from 0 to 4 positions of the phenoxy portion of Formula VII and is independently chosen from hydroxyl, $C_{1-12}$ hydrocarbyl, $C_1$-$C_{12}$ alkoxyl, $C_1$-$C_{12}$ alkoxyester, and $C_1$-$C_{12}$ acyl. Such 2-(2-Hydroxyphenyl)-1,3,5-triazines include, but are not limited to, 4,6-bis-(2,4-dimethylphenyl)-2-(2-hydroxy-4-octyloxyphenyl)-s-triazine (CYASORB® 1164 available from Cytec Industries Inc.); 4,6-bis-(2,4-dimethylphenyl)-2-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxy-ethoxy)phenyl]-6-(4-chlorophenyl)-s-triazine; 2,4-bis[2-hydroxy-4-(2-hydroxy-4-(2-hydroxy-ethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy) phenyl]-6-(4-chlorophenyl)-s-triazine; 2,4-bis(2,4-dihydroxyphenyl)-6-(2,4-dimethylphenyl)-s-triazine; 2,4-bis(4-biphenylyl)-6-[2-hydroxy-4-[(octyloxycarbonyl) ethylideneoxy]phenyl]-s-triazine; 2,4-bis(4-biphenylyl)-6-[2-hydroxy-4-(2-ethylhexyloxy)phenyl]-s-triazine; 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)phenyl]-s-triazine; 2,4-bis(2,4-dimethylphenyl)-6-[2-hydroxy-4(-3-benzyloxy-2-hydroxypropyloxy) phenyl]-s-triazine; 2,4-bis(2-hydroxy-4-n-butyloxyphenyl)-6-(2,4-di-n-butyloxyphenyl)-s-triazine; 2,4-bis(2,4-dimethylphenyl)-6-[2-hydroxy-4-(3-nonyloxy-2-hydroxypropylox-y)-5-α-cumylphenyl]-s-triazine; methylenebis-{2,4-bis(2,4-dimethylphenyl)-6-[2-hydroxy-4-(3-butyloxy-2-hydroxypropoxy)phenyl]-s-triazine}; methylene bridged dimer mixture bridged in the 3:5', 5:5' and 3:3' positions in a 5:4:1 ratio; 2,4,6-tris(2-hydroxy-4-isooctyloxycarbonyliso-propylideneoxy-phenyl)-s-triazine; 2,4-bis(2,4-dimethylphenyl)-6-(2-hydroxy-4-hexyloxy-5-α-cumylphenyl)-s-triazine; 2-(2,4,6-trimethylphenyl)-4,6-bis [2-hydroxy-4-(3-butyloxy-2-hydroxypropyloxy)phenyl]-s-triazine; 2,4,6-tris[2-hydroxy-4-(3-sec-butyloxy-2-hydroxypropyloxy)-phenyl]-s-triazine; mixture of 4,6-bis-(2,4-dimethylphenyl)-2-(2-hydroxy-4-(3-dodecyloxy-2-hydroxypropoxy)phenyl)-s-triazine and 4,6-bis-(2,4-dimethylphenyl)-2-(2-hydroxy-4-(3-tridecyloxy-2-hydroxypropoxy)phenyl)-s-triazine (TINUVIN® 400 available from BASF Corp.); 4,6-bis-(2,4-dimethylphenyl)-2-(2-hydroxy-4(3-(2-ethylhexyloxy)-2-hydroxypropoxy)-phenyl)-s-triazine; 4,6-diphenyl-2-(4-hexyloxy-2-hydroxyphenyl)-s-triazine; 2-(4,6-Diphenyl-1,3,5-triazin-2-yl)-5-[2-(2-ethylhexanoyloxy)ethoxy]phenol (ADK STAB® LA-46 available from Adeka Palmarole, Saint-Louis, France); 2,4, 6-tris(2-hydroxy-4-octyloxyphenyl)-1,3,5-triazine; propanoic acid, 2,2',2''-[1,3,5-triazine-2,4,6-triyltris[(3-hydroxy-4,1-phenylene)oxy]]tris-1,1',1''-trioctyl ester (TINUVIN® 477 available from BASF Corp.); propanoic acid, 2-[4-[4,6-bis([1,1'-biphenyl]-4-yl)-1,3,5-triazin-2yl]-3-hydroxyphenoxyl]-isooctyl ester (TINUVIN® 479 available from BASF Corp.); and combinations thereof. Other triazine compounds suitable for use with the present invention include those described in EP 1 308 084 (such as formula IId), and in U.S. patent application Ser. No. 13/144, 861 (Publication No. 2011/0272648).

In certain embodiments, the stabilizer compositions according to the invention include a blend of at least one hindered amine light stabilizer and at least one ultraviolet light absorber.

Antioxidants suitable for use with the stabilizer compositions according to the invention include any of those antioxidants conventionally known in the art. Particularly suitable antioxidants include any of those listed in U.S. Pat. No. 6,444,733. In certain embodiments, the stabilizer compositions according to the present invention can further include a tocopherol compound (e.g., α-tocopherol, β-tocopherol, γ-tocopherol, δ-tocopherol, isomers thereof, and mixtures thereof), and/or a tocotrienol compound (e.g., α, β, γ, δ-tocotrienol, isomers thereof, and mixtures thereof).

Further embodiments of the stabilizer compositions according to the invention include at least one compound chosen from:

a hydroxylamine compound according to Formula VIII:

wherein $T_1$ is chosen from $C_1$-$C_{36}$ hydrocarbyl, $C_5$-$C_{12}$ cycloalkyl, and $C_7$-$C_9$ aralkyl, optionally substituted; and $T_2$ is chosen from hydrogen or $T_1$; and a tertiary amine oxide compound according to Formula IX:

wherein $W_1$ and $W_2$ are each independently chosen from a $C_6$-$C_{36}$ hydrocarbyl chosen from a straight or branched chain $C_6$-$C_{36}$ alkyl, $C_6$-$C_{12}$ aryl, $C_7$-$C_{36}$ aralkyl, $C_7$-$C_{36}$ alkaryl, $C_5$-$C_{36}$ cycloalkyl, $C_6$-$C_{36}$ alkcycloalkyl; and $C_6$-$C_{36}$ cycloalkylalkyl;

$W_3$ is chosen from a $C_1$-$C_{36}$ hydrocarbyl chosen from a straight or branched chain $C_1$-$C_{36}$ alkyl, $C_6$-$C_{12}$ aryl, $C_7$-$C_{36}$ aralkyl, $C_7$-$C_{36}$ alkaryl, $C_5$-$C_{36}$ cycloalkyl, $C_6$-$C_{36}$ alkcycloalkyl; and $C_6$-$C_{36}$ cycloalkylalkyl; with the proviso that at least one of $W_1$, $W_2$ and $W_3$ contains a β carbon-hydrogen bond; and wherein said alkyl, aralkyl, alkaryl, cycloalkyl, alkcycloalkyl and cycloalkylalkyl groups may be interrupted by one to sixteen —O—, —S—, —SO—, —SO$_2$—, —COO—, —OCO—, —CO—, —NW$_4$—, —CONW$_4$— and —NW$_4$CO— groups, or wherein said alkyl, aralkyl, alkaryl, cycloalkyl, alkcycloalkyl and cycloalkylallyl groups may be substituted by one to sixteen groups selected from —OW$_4$, —SW$_4$, —COOW$_4$, —OCOW$_4$, —COW$_4$, —N(W$_4$)$_2$, —CON(W$_4$)$_2$, —NW$_4$COW$_4$ and 5- and 6-membered rings containing the —C(CH$_3$)(CH$_2$R$_x$)NL(CH$_2$R$_x$) (CH$_3$)C— group or wherein said alkyl, aralkyl, alkaryl, cycloalkyl, alkcycloalkyl and cycloalkylalkyl groups are both interrupted and substituted by the groups mentioned above; and wherein $W_4$ is chosen from hydrogen or $C_1$-$C_8$ alkyl;

$R_x$ is chosen from hydrogen or methyl; and

L is chosen from a $C_1$-$C_{30}$ alkyl, a —C(O)R moiety wherein R is a $C_1$-$C_{30}$ straight or branched chain alkyl group, or a —OR moiety wherein R is a $C_1$-$C_{30}$ straight or branched chain alkyl group; and wherein said aryl groups may be substituted by one to three halogen, $C_1$-$C_8$ alkyl, $C_1$-$C_8$ alkoxy or combinations thereof.

In particular embodiments, preference is given to N,N-dihydrocarbylhydroxylamine compounds according to Formula VIII wherein $T_1$ and $T_2$ are independently chosen from benzyl, ethyl, octyl, lauryl, dodecyl, tetradecyl, hexadecyl, heptadecyl and octadecyl; or wherein $T_1$ and T are each the alkyl mixture found in hydrogenated tallow amine.

In certain embodiments, hydroxylamine compounds according to Formula VIII are chosen from: N,N-dibenzylhydroxylamine; N,N-diethylhydroxylamine; dioctylhydroxylamine; N,N-dilaurylhydroxylamine; N,N-didodecylhydroxylamine; N,N-ditetradecylhydroxylaamine; N,N-dihexadecylhydroxylamine; N,N-dioctadecylhydroxylamine; N-hexadecyl-N-tetradecylhydroxylamine; N-hexadecyl-N-heptadecylhydroxylamine; N-hexadecyl-N-octadecylhydroxylamine; N-heptadecyl-N-octadecylhydroxylamine; N,N-di(hydrogenated tallow) hydroxylamine; and N,N-di(alkyl)hydroxylamine produced by the direct oxidation of N,N-di(hydrogenated tallow) amine.

In certain embodiments, preference is given to those structures of Formula IX where $W_1$ and $W_2$ are independently benzyl or substituted benzyl. It is also possible for each of $W_1$, $W_2$, and $W_3$ to be the same residue. In other embodiments, $W_1$ and $W_2$ can be alkyl groups of 8 to 26 carbon atoms, more preferably alkyl groups of 10 to 26 carbon atoms. $W_3$ can be an alkyl group of 1 to 22 carbon atoms, more preferably methyl or substituted methyl. Other preferred amine oxides include those wherein $W_1$, $W_2$, and $W_3$ are the same alkyl groups of 6 to 36 carbon atoms. Preferably, all of the aforementioned residues for $W_1$, $W_2$, and $W_3$ are saturated hydrocarbon residues or saturated hydrocarbon residues containing at least one of the aforementioned —O—, —S—, —SO—, —CO$_2$—, —CO—, or —CON— moieties. Those skilled in the art will be able to envision other useful residues for each of $W_1$, $W_2$, and $W_3$ without detracting from the present invention.

The saturated amine oxides may also include poly(amine oxides). By poly(amine oxide) is meant tertiary amine oxides containing at least two tertiary amine oxides per molecule. Illustrative poly(amine oxides), also called "poly (tertiary amine oxides)", include, but are not limited to, the tertiary amine oxide analogues of aliphatic and alicyclic diamines such as, for example, 1,4-diaminobutane; 1,6-diaminohexane; 1,10-diaminodecane; and 1,4-diaminocyclohexane, and aromatic based diamines such as, for example, diamino anthraquinones and diaminoanisoles.

Suitable amine oxides for use with the invention also include tertiary amine oxides derived from oligomers and polymers of the aforementioned diamines. Useful amine oxides also include amine oxides attached to polymers, for example, polyolefins, polyacrylates, polyesters, polyamides, polystyrenes, and the like. When the amine oxide is attached to a polymer, the average number of amine oxides per polymer can vary widely as not all polymer chains need to contain an amine oxide. All of the aforementioned amine oxides may optionally contain at least one —O—, —S—, —SO—, —CO$_2$—, —CO—, or —CONW$_4$— moiety. In a preferred embodiment, each tertiary amine oxide of the polymeric tertiary amine oxide contains a $C_1$ residue.

The groups W1, W2 and W3 of Formula IX may be attached to a molecule containing a hindered amine. Hindered amines are known in the art and the amine oxide of the present invention may be attached to the hindered amine in any manner and structural position of the hindered amine. Useful hindered amines when part of an amine oxide compound include those of the general Formulas X and XI:

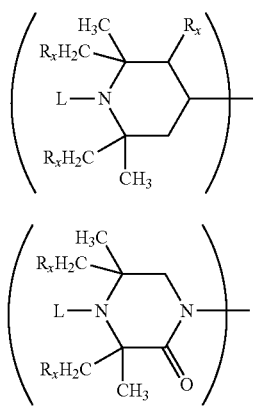

wherein L and $R_x$ are defined as described above.

Also included are amine oxides containing more than one hindered amine and more than one saturated amine oxide per molecule. The hindered amine may be attached to a poly (tertiary amine oxide) or attached to a polymeric substrate, as discussed above.

The hydroxyl amine derivatives and/or amine oxide derivatives can be used in amounts, in total, of about 0.0005% to about 5%, in particular from about 0.001% to about 2%, typically from about 0.01% to about 2% by weight, based on the weight of the organic material to be stabilized.

In other embodiments, the stabilizer compositions include further optional additives that can include at least one compound chosen from co-additives; nucleating agents; fillers; reinforcing agents; and combinations thereof.

Examples of such additives include, but are not limited to:

Basic co-additives, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zinc pyrocatecholate;

Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers);

Fillers and reinforcing agents, for example, calcium carbonate, silicates, glass fibres, glass bulbs, asbestos, talc, kaolin, mica, barium sulfate, metal oxides and hydroxides (e.g., aluminium hydroxide or magnesium hydroxide, carbon black, graphite, wood flour and flours or fibers of other natural products, synthetic fibers; impact modifiers;

Benzofuranones and indolinones, for example those disclosed in U.S. Pat. Nos. 4,325,863; 4,338,244; 5,175,312; 5,216,052; 5,252,643; 5,369,159; 5,488,117; 5,356,966; 5,367,008; 5,428,162; 5,428,177; 5,516,920; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one;

Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide;

Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-di(hydrogenated tallow)hydroxylamine;

Thiosynergists, for example, dilauryl thiodipropionate or distearyl thiodipropionate; and Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

Other additives suitable for use with the present invention that would not markedly impair the properties of the organic material to be stabilized are known to those of ordinary skill in the art and can include, for example, plasticisers, lubricants, emulsifiers, pigments, rheology additives, catalysts, flow-control agents, optical brighteners, flameproofing agents, antistatic agents, clarifying agents and blowing agents.

In certain embodiments, the stabilizer composition is present from 0.001 to 65.0% by weight based on the total weight of the organic material composition to be stabilized and based on the number and type of stabilizing additives being added and/or the characteristics of the material to be stabilized. In some embodiments, the stabilizer composition is present from 0.01 to 50% by weight of the total weight of the organic material, and preferably from 0.05 to 25% by weight of the total, or from 0.1 to 10% by weight of the total. Those of ordinary skill in the art will be able to readily determine the amount and type of stabilizing additive(s) that should be added based on preparations as known and/or described in the literature, or through no more than routine experimentation.

The stabilizer compositions according to the invention can be readily blended with the organic material to be stabilized by any suitable method known to those of skill in the art. In certain embodiments, the components of the stabilizer compositions are mixed with the material to be stabilized by at least one technique chosen from extruding, pelletizing, grinding, and molding. In other embodiments, mixing can be performed by at least one of melting, dissolution in a solvent, direct mixing, and dry mixing.

The incorporation of components for the stabilizer composition and optional further additives into the organic material to be stabilized is carried out by any suitable method known to those of skill in the art, for example before or after molding or also by applying the dissolved or dispersed stabilizer mixture to the organic material to be stabilized, with or without subsequent evaporation of the solvent. The stabilizer components and optional further additives can also be added to the organic material to be stabilized in the form of a masterbatch.

Components of the stabilizer composition and optional further additives can also be added before or during, for example, polymerization or before crosslinking. They can also be incorporated into the organic material to be stabilized in pure form (i.e., neat and directly to the resin) or encapsulated in waxes, oils or polymers. Various additives can also be preblended (i.e., mixed together) for simple addition to the organic material to be stabilized. Components of the stabilizer composition and optional further additives can also be sprayed onto the organic material to be stabilized. They are able to dilute other additives (for example the conventional additives indicated above) or their melts so that they can be sprayed also together with these additives onto the materials to be stabilized. In the case of spherically polymerized polymers it may, for example, be advantageous to apply components of the stabilizer composition optionally together with other additives, by spraying.

Reference has been made to use of the stabilizer compositions according to the present invention for stabilizing an organic material. Accordingly, another aspect of the present invention provides: (i) processes for stabilizing an organic material subject to degradation and/or discoloration due to effects from light, oxygen, and/or heat; (ii) processes for enhancing the processing stability of an organic material; and (iii) processes for reducing or preventing discoloration of an organic material. These processes are each achieved by adding before, during, or after processing a stabilizing amount of a stabilizer composition according to the invention as described throughout the specification and claims to the organic material to be stabilized. In certain embodiments, a masterbatch composition containing the stabilizer composition according to the invention will be added to the organic material to be stabilized.

Various nonliving organic materials suitable for stabilizing include, but are not limited to, polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, acrylonitrile-butadiene-styrene, styrene acrylonitrile, acrylate styrene acrylonitrile, cellulosic acetate butyrate, cellulosic polymers, polyimides, polyamideimides, polyetherimides, polyphenylsulfides, polyphenyloxidepolysulfones, polyethersulfones, polyvinylchlorides, polycarbonates, polyketones, aliphatic polyketones, thermoplastic olefins, aminoresin cross-linked polyacrylates and polyesters, polyisocyanate cross-linked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, fibers, waxes, and inks.

In certain embodiments, the nonliving organic material to be stabilized is a polyolefin. Examples of polyolefins suitable for such use with the stabilizer composition according to the invention include at least the following:

(A) Polymers of monoolefins, for example polypropylene, polyisobutylene, polybut-1-ene, and poly-4-methylpent-1-ene, polymers of diolefins such as polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE);

(B) Polyolefins, i.e. the polymers of monoolefins exemplified in (A), preferably polyethylene and polypropylene, can be prepared by different, and especially by the following, methods:

i) radical polymerisation (normally under high pressure and at elevated temperature); or ii) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC);

(C) Mixtures of the polymers mentioned under (A), for example mixtures of polypropylene with polyisobutylene, polypropylene with polyethylene (for example PP/HDPE, PP/LDPE) and mixtures of different types of polyethylene (for example LDPE/HDPE); and (D) Copolymers of monoolefins and diolefins with each other or with other vinyl monomers, for example ethylene/propylene copolymers, linear low density polyethylene (LL-DPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in (A) above, for example polypropylene/ethylene-propylene copolymers, LDPE/ethylene-vinyl acetate copolymers (EVA), LDPE/ ethylene-acrylic acid copolymers (EAA), LLDPE/EVA, LLDPE/EAA and alternating or random polyalkylene/carbon monoxide copolymers and mixtures thereof with other polymers, for example polyamides.

The stabilizer compositions according to the present invention are also contemplated for use in various industrial molding processes to produce stabilized molded articles. Accordingly, in another aspect the invention provides processes for producing a molded article by adding a polymeric organic material and a polymer-stabilizing amount of a stabilizer composition according to the present invention as described and claimed herein to an industrial molding apparatus or device, or otherwise within an industrial molding process, and cycling the stabilized polymeric material through the apparatus/device and thereby the molding process.

Those of skill in the art will appreciate that the compositions and processes are suitable for use with, and readily adapted to, any industrial molding process including, but not limited to, injection molding, rotomolding, blow molding, reel-to-reel molding, metal injection molding, compression molding, transfer molding, dip molding, gas assist molding, insert injection molding, micro molding, reaction injection molding, two shot injection molding, as well as any variations or combinations thereof.

In certain embodiments of the processes described herein, the stabilizer composition is present at from 0.001% to 65.0% by weight of the total weight of the organic material to be stabilized; preferably at from 0.01% to 25%; and more preferably at from 0.01% to 10% by weight of the total weight of the organic material to be stabilized.

It is also contemplated that the components of the stabilizer compositions and/or an organic material to be stabilized described herein may be contained in a kit. The kit may include single or multiple components of at least one stabilizer composition according to the invention, at least one material to be stabilized (e.g., a polymer composition such as a polyolefin), and at least one further optional additive, each packaged or formulated individually, or single or multiple components of at least one stabilizer composition according to the invention, at least one material to be stabilized, and at least one further optional additive packaged or formulated in combination. Thus, one or more components of a stabilizer composition can be present in first container, and the kit can optionally include one or more components of the stabilizer composition and/or material to be stabilized in a second or further container. The container or containers are placed within a package, and the package can optionally include administration or mixing instructions in the form of a label or website address on the package, or in the form of an insert included in the packaging of the kit. A kit can include additional components or other means for administering or mixing the components as well as solvents or other means for formulation.

Other Embodiments

1. A stabilizer composition comprising a stabilizing amount of a chroman-based compound according to Formula (V):

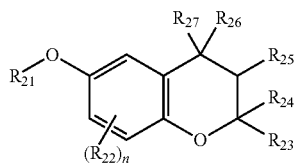

(V)

wherein $R_{21}$ is chosen from $COR_{28}$ or $Si(R_{29})_3$, wherein $R_{28}$ is chosen from H or a $C_1$-$C_{20}$ hydrocarbyl; and $R_{29}$ is chosen from a $C_1$-$C_{12}$ hydrocarbyl or alkoxy;

$R_{22}$ is a substituent that can be the same or different at from n=0 to 3 positions of the aromatic portion of Formula V and is independently chosen from H or a $C_1$-$C_{12}$ hydrocarbyl;

$R_{23}$ is chosen from H or a $C_1$-$C_{12}$ hydrocarbyl;

$R_{24}$ is chosen from H or a $C_1$-$C_{20}$ hydrocarbyl; and each of $R_{25}$-$R_{27}$ is independently chosen from a member selected from the group consisting of H; a $C_1$-$C_{12}$ hydrocarbyl; and $OR_{30}$, wherein $R_{30}$ is chosen from H or a $C_1$-$C_{12}$ hydrocarbyl; and $R_{27}$ is H, or a bond which together with $R_{26}$ forms =O.

2. A stabilizer composition according to embodiment 1 further comprising at least one compound chosen from the group of organic phosphites or phosphonites.

3. A stabilizer composition according to embodiment 2, wherein the at least one organic phosphite or phosphonite is chosen from a compound according to Formulas 1-7:

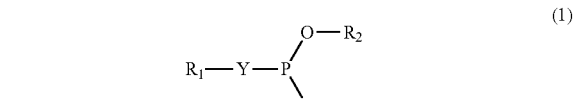

(1)

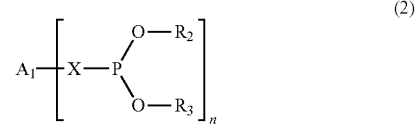

(2)

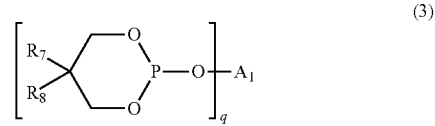

(3)

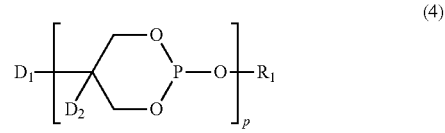

(4)

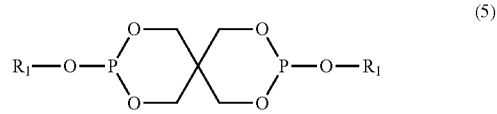

(5)

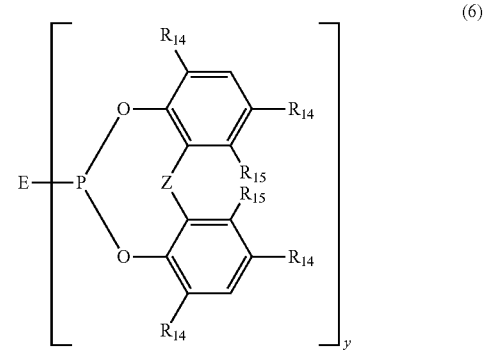

(6)

-continued

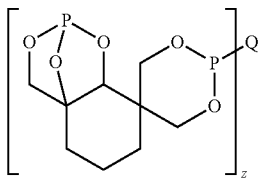

(7)

in which the indices are integral and
n is 2, 3 or 4; p is 1 or 2; q is 2 or 3; r is 4 to 12; y is 1, 2 or 3; and z is 1 to 6;
$A_1$, if n is 2, is $C_2$-$C_{18}$ alkylene; $C_2$-$C_{12}$ alkylene interrupted by oxygen, sulfur or —$NR_4$—; a radical of the formula

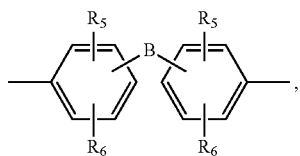

or phenylene;
$A_1$, if n is 3, is a radical of the formula —$C_rH_{2r-1}$—;
$A_1$, if n is 4, is

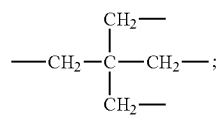

$A_2$ is as defined for $A_1$ if n is 2;
B is a direct bond, —$CH_2$—, —$CHR_4$—, —$CR_1R_4$—, sulfur, $C_5$-$C_7$ cycloalkylidene, or cyclohexylidene which is substituted by from 1 to 4 $C_1$-$C_4$ alkyl radicals in position 3, 4 and/or 5;
$D_1$, if p is 1, is $C_1$-$C_4$ alkyl and, if p is 2, is —$CH_2OCH_2$—;
$D_2$, if p is 1, is $C_1$-$C_4$ alkyl;
E, if y is 1, is $C_1$-$C_{18}$ alkyl, —$OR_1$ or halogen;
E, if y is 2, is —O-$A_2$-O—,
E, if y is 3, is a radical of the formula $R_4C(CH_2O—)_3$ or $N(CH_2CH_2O—)_3$;
Q is the radical of an at least z-valent alcohol or phenol, this radical being attached via the oxygen atom to the phosphorus atom;
$R_1$, $R_2$ and $R_3$ independently of one another are $C_1$-$C_{18}$ alkyl which is unsubstituted or substituted by halogen, —$COOR_4$, —CN or —$CONR_4R_4$; $C_2$-$C_{18}$ alkyl interrupted by oxygen, sulfur or —$NR_4$—; $C_7$-$C_9$ phenylalkyl; $C_5$-$C_{12}$ cycloalkyl, phenyl or naphthyl; naphthyl or phenyl substituted by halogen, 1 to 3 alkyl radicals or alkoxy radicals having a total of 1 to 18 carbon atoms or by $C_7$-$C_9$ phenylalkyl; or a radical of the formula

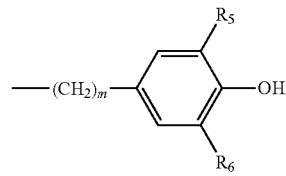

in which m is an integer from the range 3 to 6;
$R_4$ is hydrogen, $C_1$-$C_8$ alkyl, $C_5$-$C_{12}$ cycloalkyl or $C_7$-$C_9$ phenylalkyl,
$R_5$ and $R_6$ independently of one another are hydrogen, $C_1$-$C_8$ alkyl or $C_5$-$C_6$ cycloalkyl,
$R_7$ and $R_8$, if q is 2, independently of one another are $C_1$-$C_4$ alkyl or together are a 2,3-dehydropentamethylene radical; and
$R_7$ and $R_8$, if q is 3, are methyl;
$R_{14}$ is hydrogen, $C_1$-$C_9$ alkyl or cyclohexyl,
$R_{15}$ is hydrogen or methyl and, if two or more radicals $R_{14}$ and $R_{15}$ are present, these radicals are identical or different,
X and Y are each a direct bond or oxygen,
Z is a direct bond, methylene, —$C(R_{16})_2$— or sulfur, and
$R_{16}$ is $C_1$-$C_8$ alkyl;
a trisarylphosphite according to Formula 8:

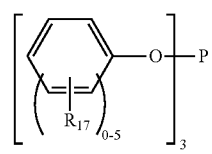

(8)

wherein $R_{17}$ is a substituent that is the same or different at from 0 to 5 positions of the aromatic portion of Formula 8 and is independently chosen from a member selected from the group consisting of $C_1$-$C_{20}$ alkyl, $C_3$-$C_{20}$ cycloalkyl, $C_4$-$C_{20}$ alkyl cycloalkyl, $C_6$-$C_{10}$ aryl, and $C_7$-$C_{20}$ alkylaryl; and combinations thereof.

4. A stabilizer composition according to embodiment 3, wherein the organic phosphite or phosphonite is chosen from: triphenyl phosphite; diphenyl alkyl phosphites; phenyl dialkyl phosphites; trilauryl phosphite; trioctadecyl phosphite; distearyl pentaerythritol phosphite; tris(2,4-di-tert-butylphenyl)phosphite; tris(nonylphenyl)phosphite; a compound of formulae (A), (B), (C), (D), (E), (F), (G), (H), (J), (K) and (L):

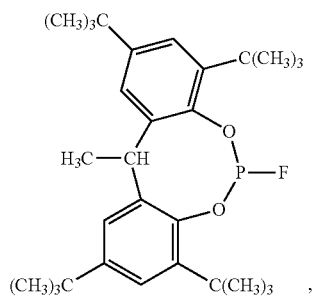
(A)
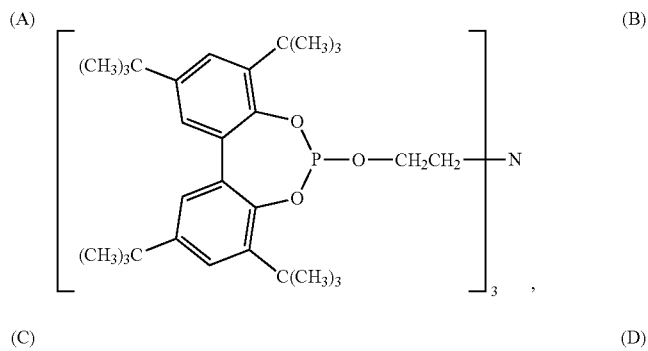
(B)
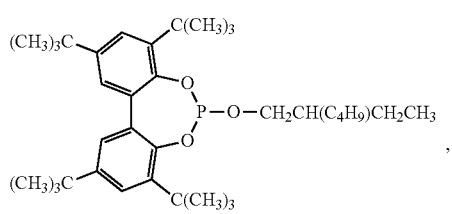
(C)
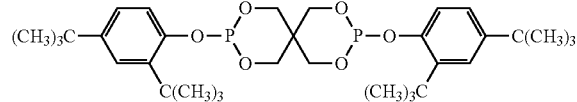
(D)
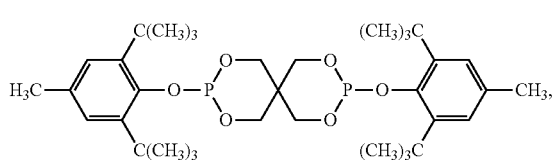
(E)
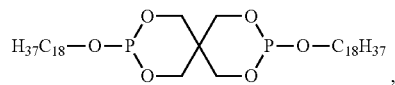
(F)
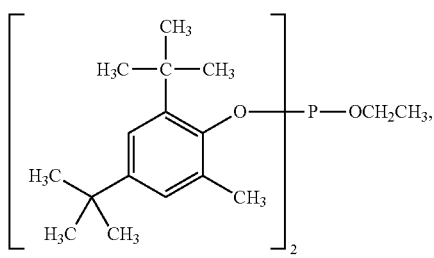
(G)
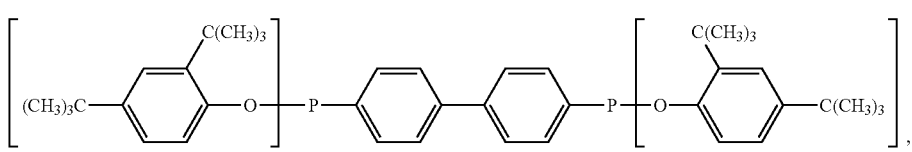
(H)
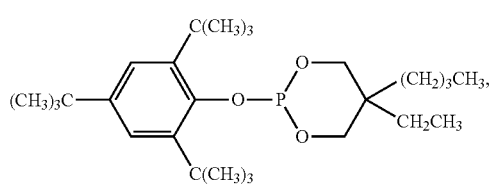
(J)
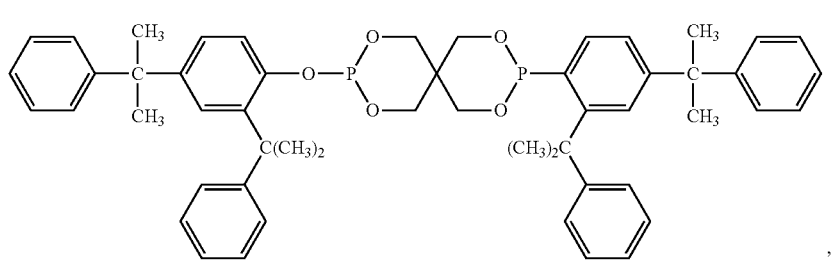
(K)

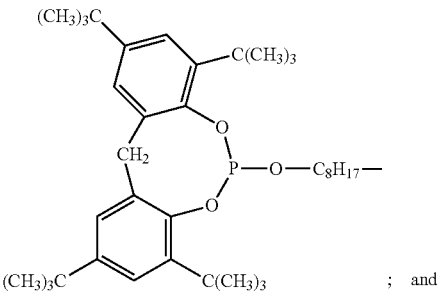

(L)

2-butyl-2-ethyl-1,3-propanediol 2,4,6-tri-t-butylphenol phosphite, bis-(2,6-di-t-butyl-4-methlphenyl)pentaerythritol diphosphite, 2-butyl-2-ethyl-1,3-propanediol 2,4-di-cumylphenol phosphite, 2-butyl-2-ethyl-1,3-propanediol 4-methyl-2,6-di-t-butylphenol phosphite, and bis-(2,4,6-tri-t-butyl-phenyl)pentaerythritol diphosphite.

5. A stabilizer composition according to any one of embodiments 3-4, wherein the at least one organic phosphite or phosphonite is chosen from tris(2,4-di-tert-butylphenyl) phosphite (IRGAFOS® 168); Bis(2,4-dicumylphenyl)pentaerythritol diphosphite (DOVERPHOS® S9228); and tetrakis(2,4-di-tert-butylphenyl)-4,4'-biphenylene-diphosphonite (IRGAFOS® P-EPQ).

6. A stabilizer composition according to any one of the preceding embodiments further comprising at least one hindered phenol compound.

7. A stabilizer composition according to embodiment 6, wherein the at least one hindered phenol compound comprises a molecular fragment according to one or more of Formula (IVa), (IVb), or (IVc):

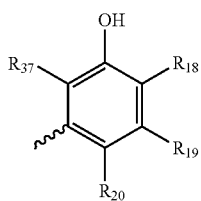
(IVa)

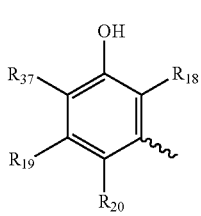
(IVb)

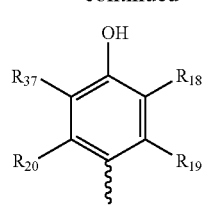
(IVc)

wherein $R_{18}$ is chosen from hydrogen or a $C_{1-4}$ hydrocarbyl;

each of $R_{19}$ and $R_{20}$ is independently chosen from hydrogen or a $C_1$-$C_{20}$ hydrocarbyl; and $R_{37}$ is chosen from a $C_1$-$C_{12}$ hydrocarbyl.

8. A stabilizer composition according to embodiment 7, wherein each of $R_{18}$ and $R_{37}$ is independently chosen from methyl or t-butyl.

9. A stabilizer composition according to any one of embodiments 6-8, wherein the at least one hindered phenol compound is chosen from a member selected from the group consisting of (1,3,5-Tris(4-t-butyl-3-hydroxy-2,6-dimethylbenzyl)-1,3,5-triazine-2,4,6-(1H,3H,5H)-trione; 1,1,3-Tris (2'-methyl-4'-hydroxy-5'-t-butylphenyl)butane; Triethylene glycol bis[3-(3-t-butyl-4-hydroxy-5-methylphenyl)propionate]; 4,4'-Thiobis(2-t-butyl-5-methylphenol); 2,2'-Thiodiethylene bis[3-(3-t-butyl-4-hydroxyl-5-methylphenyl)propionate]; Octadecyl 3-(3'-t-butyl-4'-hydroxy-5'-methylphenyl) propionate; Tetrakismethylene(3-t-butyl-4-hydroxy-5-methylhydrocinnamate)methane; N,N'-Hexamethylene bis [3-(3-t-butyl-4-hydroxy-5-methylphenyl)propionamide]; Di(4-tertiarybutyl-3-hydroxy-2,6-dimethyl benzyl)thiodipropionate; and octadecyl 3,5-di-(tert)-butyl-4-hydroxyhydrocinnamate.

10. A stabilizer composition according to any one of the preceding embodiments, wherein $R_{22}$ is present in at least one instance and is methyl.

11. A stabilizer composition according to any one of the preceding embodiments, wherein $R_{24}$ is a $C_1$-$C_{18}$ hydrocarbyl.

12. A stabilizer composition according to any one of the preceding embodiments, wherein the chroman-based compound is vitamin E acetate according to Formula (Va)

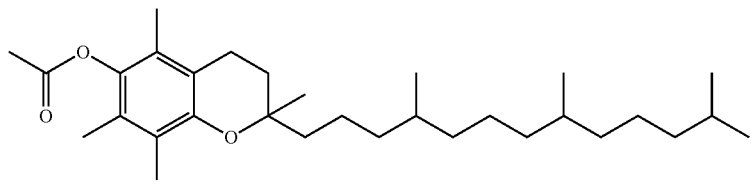

(Va)

or isomers and/or mixtures thereof.

13. A stabilizer composition according to any one of the preceding embodiments, wherein the chroman-based compound is a blend of compounds comprising a chroman-based compound according to Formula V and another chroman-based compound.

14. A stabilizer composition according to any one of the preceding embodiments, wherein the chroman-based compound is present from 0.001 to 5.0% by weight of the total weight of the stabilizer composition.

15. A stabilizer composition according to embodiments 14, wherein the chroman-based compound is present from 0.01 to 1.0% by weight of the total weight of the stabilizer composition.

16. A stabilizer composition according to any one of the preceding embodiments further comprising an effective amount of a light stabilizer chosen from a member selected from the group consisting of hindered amine light stabilizers, hindered hydroxyl benzoates, nickel phenolates, ultraviolet light stabilizers, and combinations thereof.

17. A stabilizer composition according to embodiments 16, wherein the light stabilizer is a hindered amine light stabilizer compound comprising a molecular fragment according to Formula (VI):

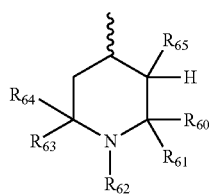

(VI)

wherein $R_{62}$ is chosen from a member selected from the group consisting of hydrogen; OH; $C_1$-$C_{20}$ hydrocarbyl; —$CH_2CN$; $C_1$-$C_{12}$ acyl; and $C_1$-$C_{18}$ alkoxy;

$R_{65}$ is chosen from a member selected from the group consisting of hydrogen; and $C_1$-$C_8$ hydrocarbyl; and each of $R_{60}$, $R_{61}$, $R_{63}$, and $R_{64}$ is independently chosen from a $C_1$-$C_{20}$ hydrocarbyl, or $R_{60}$ and $R_{61}$ and/or $R_{63}$ and $R_{64}$ taken together with the carbon to which they are attached form a $C_5$-$C_{10}$ cycloalkyl;

or Formula (VIa)

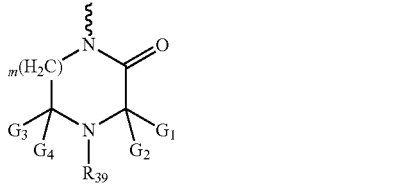

(VIa)

wherein m is an integer from 1 to 2;

$R_{39}$ is chosen from a member selected from the group consisting of hydrogen; OH; $C_1$-$C_{20}$ hydrocarbyl; —$CH_2CN$; $C_1$-$C_{12}$ acyl; and $C_1$-$C_{18}$ alkoxy; and each of $G_1$-$G_4$ is independently chosen from a $C_1$-$C_{20}$ hydrocarbyl.

18. A stabilizer composition according to embodiment 16 or 17, wherein the hindered amine light stabilizer is chosen from a member selected from the group consisting of bis(2,2,6,6-tetramethylpiperidin-4-yl)sebacate; bis(2,2,6,6-tetramethylpiperidin-4-yl)succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl)n-butyl 3,5-di-tert-butyl-4-hydroxybenzylmalonate; a condensate of 1-(2-hydroxyethyl)-2,2,6,6-tetramethyl-4-hydroxypiperidine and succinic acid; 2,2,6,6-tetramethylpiperidin-4-yl stearate; 2,2,6,6-tetramethylpiperidin-4-yl dodecanate; 1,2,2,6,6-pentamethylpiperidin-4-yl stearate; 1,2,2,6,6-pentamethylpiperidin-4-yl dodecanate; a condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl)nitrilotriacetate; tetrakis(2,2,6,6-tetramethylpiperidin-4-yl)-1,2,3,4-butanetetracarboxylate; 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; a condensate of N,N'-bis(2,2,6,6-tetramethylpiperidin-4-yl)hexamethylenediamine and 4-morpholino-2,6-dichloro-1,3,5-triazine; a condensate of 2-chloro-4,6-bis(4-n-butylamino-2,2,6,6-tetramethylpiperidyl)-1,3,5-triazine and 1,2-bis(3-aminopropylamino)ethane; a condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; a condensate of N,N'-bis(2,2,6,6-tetramethylpiperidin-4-yl)hexamethylenediamine and 4-cyclohexylamino-2,6-dichloro-1,3,5-triazine; a condensate of 1,2-bis(3-aminopropylamino)ethane, 2,4,6-trichloro-1,3,5-triazine and 4-butylamino-2,2,6,6-tetramethylpiperidine; 2-undecyl-7,7,9,9-tetramethyl-1-oxa-3,8-diaza-4-oxospiro[4.5]decane; oxo-piperanzinyl-triazines; a reaction product of 7,7,9,9-tetramethyl-2-cycloundecyl-1-oxa-3,8-diaza-4-oxospiro[4.5]decane and epichlorohydrin; tetrakis(2,2,6,6-tetramethyl-4-piperidyl)butane-1,2,3,4-tetracarboxylate; 1,2,3,4-butanetetracarboxylic acid, tetrakis(1,2,2,6,6-pentamethyl-4-piperidinyl)ester; 1,2,3,4-butanetetracarboxylic acid, 1,2,2,6,6-pentamethyl-4-piperidinyl tridecyl ester; 1,2,3,4-butanetetracarboxylic acid, 2,2,6,6-tetramethyl-4-piperidinyl tridecyl ester; 1,2,3,4-butanetetracarboxylic acid, polymer with 2,2,6,6-tetramethyl-2,4,8,10-tetraoxaspiro[5.5]-undecane-3,9-diethanol,1,2,2,6,6-pentamethyl-4-piperidinyl ester; 1,2,3,4-butanetetracarboxylic acid, polymer with 2,2,6,6-tetramethyl-2,4,8,10-tetraoxaspiro[5.5]-undecane-3,9-diethanol, 2,2,6,6-tetramethyl-4-piperidinyl ester; bis(1-undecanoxy-2,2,6,6-tetramethylpiperidin-4-yl) carbonate; 1-(2-hydroxy-2-methylpropoxy)-2,2,6,6-tetramethyl-4-piperidinol; 1-(2-hydroxy-2-methylpropoxy)-4-octadecanoyloxy-2,2,6,6-tetramethylpiperidine; 1-(4-octadecanoyloxy-2,2,6,6-tetramethylpiperidin-1-yloxy)-2-octadecanoyloxy-2-methylpropane; 1-(2-hydroxyethyl)-2,2,6,6-tetramethyl-4-piperidinol; a reaction product of 1-(2-hydroxyethyl)-2,2,6,6-tetramethyl-4-piperidinol and dimethylsuccinate; 2,2,4,4-tetramethyl-7-oxa-3,20-diazadispiro[5.1.11.2]heneicosan-21-one; the ester of 2,2,6,6-tetramethyl-4-piperidinol with higher fatty acids; 3-dodecyl-1-(2,2,6,6-tetramethyl-4-piperidyl)pyrrolidine-2,5-dione; 1H-Pyrrole-2,5-dione, 1-octadecyl-, polymer with (1-methylethenyl)benzene and 1-(2,2,6,6-tetramethyl-4-piperidinyl)-1H-pyrrole-2,5-dione; piperazinone, 1,1',1''-[1,3,5-triazine-2,4,6-triyltris[(cyclohexylimino)-2,1-ethanediyl]] tris[3,3,5,5-tetramethyl-; piperazinone, 1,1',1''-[1,3,5-triazine-2,4,6-triyltris[(cyclohexylimino)-2,1-ethanediyl]] tris[3,3,4,5,5-pentamethyl-; the reaction product of 7,7,9,9-tetramethyl-2-cycloundecyl-1-oxa-3,8-diaza-4-oxospiro[4.5]decane and epichlorohydrin; the condensate of N,N'-bis(2,2,6,6-tetramethylpiperidin-4-yl) hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 2-[(2-hydroxyethyl)amino]-4,6-bis[N-(1-cyclohexyloxy-2,2,6,6-tetramethylpiperidin-4-yl)butylamino-1,3,5-triazine; propanedioic acid, [(4-methoxyphenyl)-methylene]-bis-(1,2,2,6,6-pentamethyl-4-piperidinyl)ester; tetrakis(2,2,6,6-tetramethylpiperidin-4-yl)-1,2,3,4-butanetetracarboxylate; benzenepropanoic acid, 3,5-bis(1,1-dimethylethyl)-4-hydroxy-, 1-[2-[3-[3,5-bis(1,1-dimethylethyl)-4-hydroxyphenyl]-1-oxopropoxy]ethyl]-2,2,6,6-tetramethyl-4-piperidinyl ester; N-(1-octyloxy-2,2,6,6-tetramethylpiperidin-4-yl)-N'-dodecyloxalamide; tris(2,2,6,6-tetramethylpiperidin-4-yl) nitrilotriacetate; 1,5-dioxaspiro{5,5}undecane-3,3-dicarboxylic acid, bis(1,2,2,6,6-pentamethyl-4-piperidinyl); 1,5-dioxaspiro{5,5}undecane-3,3-dicarboxylic acid, bis(2,2,6,6-tetramethyl-4-piperidinyl); the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; 1,2,3,4-butanetetracarboxylic acid, 1,2,2,6,6-pentamethyl-4-piperidinyl tridecyl ester; tetrakis(2,2,6,6-tetramethylpiperidin-4-yl)-1,2,3,4-butanetetracarboxylate; 1,2,3,4-butanetetracarboxylic acid, 2,2,6,6-tetramethyl-4-piperidinyl tridecyl ester; tetrakis(1,2,2,6,6-pentamethylpiperidin-4-yl)-1,2,3,4-butanetetracarboxylate; mixture of 2,2,4,4-tetramethyl-21-oxo-7-oxa-3.20-diazaspiro(5.1.11.2)-heneicosane-20-propanoic acid-dodecylester and 2,2,4,4-tetramethyl-21-oxo-7-oxa-3.20-diazaspiro(5.1.11.2)-heneicosane-20-propanoic acid-tetradecylester; 1H,4H,5H,8H-2,3a,4a,6,7a,8a-hexaazacyclopenta[def]fluorene-4,8-dione, hexahydro-2,6-bis(2,2,6,6-tetramethyl-4-piperidinyl)-; polymethyl[propyl-3-oxy(2',2',6',6'-tetramethyl-4,4'-piperidinyl)]siloxane; polymethyl[propyl-3-oxy(1',2',2',6',6'-pentamethyl-4,4'-piperidinyl)]siloxane; copolymer of methylmethacrylate with ethyl acrylate and 2,2,6,6-tetramethylpiperidin-4-yl acrylate; copolymer of mixed $C_{20}$ to $C_{24}$ alpha-olefins and (2,2,6,6-tetramethylpiperidin-4-yl)succinimide; 1,2,3,4-butanetetracarboxylic acid, polymer with β,β,β',β'-tetramethyl-2,4,8,10-tetraoxaspiro[5.5]undecane-3,9-diethanol, 1,2,2,6,6-pentamethyl-4-piperidinyl ester; 1,2,3,4-butanetetracarboxylic acid, polymer with β,β,β',β'-tetramethyl-2,4,8,10-tetraoxaspiro[5.5]undecane-3,9-diethanol, 2,2,6,6-tetramethyl-4-piperidinyl ester copolymer; 1,3-benzenedicarboxamide, N,N'-bis(2,2,6,6-tetramethyl-4-piperidinyl; 1,1'-(1,10-dioxo-1,10-decanediyl)-bis(hexahydro-2,2,4,4,6-pentamethylpyrimidine; ethane diamide, N-(1-acetyl-2,2,6,6-tetramethylpiperidinyl)-N'-dodecyl; formamide, N,N'-1,6-hexanediylbis[N-(2,2,6,6-tetramethyl-4-piperidinyl); D-glucitol, 1,3:2,4-bis-O-(2,2,6,6-tetramethyl-4-piperidinylidene)-; 2,2,4,4-tetramethyl-7-oxa-3,20-diaza-21-oxo-dispiro[5.1.11.2]heneicosane; propanamide, 2-methyl-N-(2,2,6,6-tetramethyl-4-piperidinyl)-2-[(2,2,6,6-tetramethyl-4-piperidinyl)amino]-; 7-oxa-3,20-diazadispiro[5.1.11.2]heneicosane-20-propanoic acid, 2,2,4,4-tetramethyl-21-oxo-, dodecyl ester; N-(2,2,6,6-tetramethylpiperidin-4-yl)-β-aminopropionic acid dodecyl ester; N-(2,2,6,6-tetramethylpiperidin-4-yl)-N'-aminooxalamide; propanamide, N-(2,2,6,6-tetramethyl-4-piperidinyl)-3-[(2,2,6,6-tetramethyl-4-piperidinyl)amino]-; mixture of 4-hexadecyloxy- and 4-stearyloxy-2,2,6,6-tetramethylpiperidine; 3-dodecyl-1-(1,2,2,6,6-pentamethylpiperidin-4-yl) pyrrolidine-2,5-dione; 3-dodecyl-1-(1-ethanoyl-2,2,6,6-pentamethylpiperidin-4-yl)pyrrolidine-2,5-dione; bis(2,2,6,6-tetramethylpiperidin-4-yl)succinate; bis(1,2,2,6,6-pentamethylpiperidin-4-yl)n-butyl 3,5-di-tert-butyl-4-hydroxybenzylmalonate; tris(2,2,6,6 tetramethylpiperidin-4-yl)nitrilotriacetate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl)pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl)pyrrolidine-2,5-dione; a mixture of 4-hexadecyloxy- and 4-stearyloxy-2,2,6,6-tetramethylpiperidine; 2-undecyl-7,7,9,9-tetramethyl-1-oxa-3,8-diaza-4-oxospiro[4.5]decane; 1,5- dioxaspiro{5,5}undecane-3,3-dicarboxylic acid, bis(2,2,6,6-tetramethyl-4-piperidinyl) and 1,5-dioxaspiro{5,5}undecane-3,3-dicarboxylic acid, bis(1,2,2,6,6-pentamethyl-4-piperidinyl); N$^1$-(β-hydroxyethyl)3,3-pentamethylene-5,5-dimethylpiperazin-2-one; N$^1$-tert-octyl-3,3,5,5-tetramethyl-diazepin-2-one; N$^1$-tert-octyl-3,3-pentamethylene-5,5-hexamethylene-diazepin-2-one; N$^1$-tert-octyl-3,3-pentamethylene-5,5-dimethylpiperazin-2-one; trans-1,2-cyclohexane-bis-(N$^1$-5,5-dimethyl-3,3-pentamethylene-2-piperazinone; trans-1,2-cyclohexane-bis-(N$^1$-3,3,5,5-dispiropentamethylene-2-piperazinone); N$^1$-isopropyl-1,4-diazadispiro-(3,3,5,5)pentamethylene-2-piperazinone; N$^1$-isopropyl-1,4-diazadispiro-3,3-pentamethylene-5,5-tetramethylene-2-piperazinone; N$^1$-isopropyl-5,5-dimethyl-3,3-pentamethylene-2-piperazinone; trans-1,2-cyclohexane-bis-N$^1$-(dimethyl-3,3-pentamethylene-2-piperazinone); N$^1$-octyl-5,5-dimethyl-3,3-pentamethylene-1,4-diazepin-2-one; and N$^1$-octyl-1,4-diazadispiro-(3,3,5,5)pentamethylene-1,5-diazepin-2-one.

19. A stabilizer composition according to embodiment 16, wherein the light stabilizer is an ultraviolet light absorber chosen from a member selected from the group consisting of a 2-hydroxybenzophenone compound, a 2-(2'-hydroxyphenyl)benzotriazole compound, a 2-(2'-hydroxyphenyl)-1,3,5-triazine compound, and combinations thereof.

20. A stabilizer composition according to embodiment 19, wherein the ultraviolet light absorber is a 2-(2'-hydroxyphenyl)-1,3,5-triazine compound according to Formula (VII):

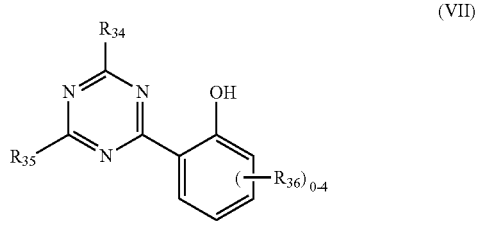

(VII)

wherein
each of R$_{34}$ and R$_{35}$ is independently chosen from a member selected from the group consisting of an optionally substituted C$_6$-C$_{10}$ aryl group, a C$_1$-C$_{10}$ hydrocarbyl-substituted amino, a C$_1$-C$_{10}$ acyl and a C$_1$-C$_{10}$ alkoxyl; and R$_{36}$ is a substituent that is the same or different at from 0 to 4 positions of the phenoxy portion of Formula VII and in each instance is independently chosen from a member selected from the group consisting of hydroxyl, a C$_1$-C$_{12}$ hydrocarbyl, a C$_1$-C$_{12}$ alkoxyl, a C$_1$-C$_{12}$ alkoxyester, and a C$_1$-C$_{12}$ acyl.

21. A stabilizer composition according to any one of embodiment 19 or embodiment 20, wherein the 2-(2'-hydroxyphenyl)-1,3,5-triazine compound is chosen from a member selected from the group consisting of 4,6-bis-(2,4-dimethylphenyl)-2-(2-hydroxy-4-octyloxyphenyl)-s-triazine (Cyasorb® 1164 available from Cytec Industries Inc.); 4,6-bis-(2,4-dimethylphenyl)-2-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxy-ethoxy)phenyl]-6-(4-chlorophenyl)-s-triazine; 2,4-bis[2-hydroxy-4-(2-hydroxy-4-(2-hydroxy-ethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine; 2,4-bis(2,4-dihydroxyphenyl)-6-(2,4-dimethylphenyl)-s-triazine; 2,4-bis(4-biphenylyl)-6-[2-hydroxy-4-[(octyloxycarbonyl)ethylideneoxy]phenyl]-s-triazine; 2,4-bis(4-biphenylyl)-6-[2-hydroxy-4-(2-ethylhexyloxy)phenyl]-s-triazine; 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)phenyl]-s-triazine; 2,4-bis(2,4-dimethylphenyl)-6-[2-hydroxy-4(-3-benzyloxy-2-hydroxypropyloxy)phenyl]-s-triazine; 2,4-bis(2-hydroxy-4-n-butyloxyphenyl)-6-(2,4-di-n-butyloxyphenyl)-s-triazine; 2,4-bis(2,4-dimethylphenyl)-6-[2-hydroxy-4-(3-nonyloxy-2-hydroxypropylox-y)-5-α-cumylphenyl]-s-triazine; methylenebis-{2,4-bis(2,4-dimethylphenyl)-6-[2-hydroxy-4-(3-butyloxy-2-hydroxypropoxy)phenyl]-s-triazine}; methylene bridged dimer mixture bridged in the 3:5', 5:5' and 3:3' positions in a 5:4:1 ratio; 2,4,6-tris(2-hydroxy-4-isooctyloxycarbonyliso-propylideneoxy-phenyl)-s-triazine; 2,4-bis(2,4-dimethylphenyl)-6-(2-hydroxy-4-hexyloxy-5-α-cumylphenyl)-s-triazine; 2-(2,4,6-trimethylphenyl)-4,6-bis[2-hydroxy-4-(3-butyloxy-2-hydroxypropyloxy)phenyl]-s-triazine; 2,4,6-tris[2-hydroxy-4-(3-sec-butyloxy-2-hydroxypropyloxy)phenyl]-s-triazine; mixture of 4,6-bis-(2,4-dimethylphenyl)-2-(2-hydroxy-4-(3-dodecyloxy-2-hydroxypropoxy)phenyl)-s-triazine and 4,6-bis-(2,4-dimethylphenyl)-2-(2-hydroxy-4-(3-tridecyloxy-2-hydroxypropoxy)phenyl)-s-triazine (Tinuvin® 400 available from Ciba Specialty Chemicals Corp.); 4,6-bis-(2,4-dimethylphenyl)-2-(2-hydroxy-4(3-(2-ethylhexyloxy)-2-hydroxypropoxy)-phenyl)-s-triazine; 4,6-diphenyl-2-(4-hexyloxy-2-hydroxyphenyl)-s-triazine; and combinations thereof.

22. A stabilizer composition according to embodiment 16, wherein the light stabilizer is a hindered amine light stabilizer according to embodiment 17 or embodiment 18, and an ultraviolet light absorber according to embodiment 20 or embodiment 21.

23. A stabilizer composition according to any one of the preceding embodiments further comprising at least one compound chosen from a member selected from the group consisting of:
a hydroxylamine compound according to Formula (VIII):

(VIII)

wherein
T$_1$ is chosen from a member selected from the group consisting of an optionally substituted C$_1$-C$_{36}$ hydrocarbyl, an optionally substituted C$_5$-C$_{12}$ cycloalkyl, and an optionally substituted C$_7$-C$_9$ aralkyl; and T$_2$ is chosen from hydrogen or T$_1$; and a tertiary amine oxide compound according to Formula (IX):

(IX)

wherein
each of W$_1$ and W$_2$ is independently chosen from a C$_6$-C$_{36}$ hydrocarbyl chosen from a member selected from the group consisting of a straight or branched chain $C_6$-$C_{36}$ alkyl, a $C_6$-$C_{12}$ aryl, a $C_7$-$C_{36}$ aralkyl, a $C_7$-$C_{36}$ alkaryl, a $C_5$-$C_{36}$ cycloalkyl, a $C_6$-$C_{36}$ alkcycloalkyl; and a $C_6$-$C_{36}$ cycloalkylalkyl;

$W_3$ is chosen from a $C_1$-$C_{36}$ hydrocarbyl chosen from a member selected from the group consisting of a straight or branched chain $C_1$-$C_{36}$ alkyl, a $C_6$-$C_{12}$ aryl, a $C_7$-$C_{36}$ aralkyl, a $C_7$-$C_{36}$ alkaryl, a $C_5$-$C_{36}$ cycloalkyl, a $C_6$-$C_{36}$ alkcycloalkyl; and a $C_6$-$C_{36}$ cycloalkylalkyl;

with the proviso that at least one of $W_1$, $W_2$ and $W_3$ contains a β carbon-hydrogen bond; and wherein said alkyl, aralkyl, alkaryl, cycloalkyl, alkcycloalkyl and cycloalkylalkyl groups may be interrupted by one to sixteen groups chosen from a member selected from the group consisting of —O—, —S—, —SO—, —SO$_2$—, —COO—, —OCO—, —CO—, —NW$_4$—, —CONW$_4$— and —NW$_4$CO—, or wherein said alkyl, aralkyl, alkaryl, cycloalkyl, alkcycloalkyl and cycloalkylallyl groups may be substituted by one to sixteen groups chosen from a member selected from the group consisting of —OW$_4$, —SW$_4$, —COOW$_4$, —OCOW$_4$, —COW$_4$, —N(W$_4$)$_2$, —CON(W$_4$)$_2$, —NW$_4$COW$_4$ and 5- and 6-membered rings containing the group —C(CH$_3$)(CH$_2$R$_x$)NL(CH$_2$R$_x$)(CH$_3$)C—, or wherein said alkyl, aralkyl, alkaryl, cycloalkyl, alkcycloalkyl and cycloalkylalkyl groups are both interrupted and substituted by the groups mentioned above; and wherein $W_4$ is chosen from hydrogen or a $C_1$-$C_8$ alkyl;

$R_x$ is chosen from hydrogen or methyl; and

L is chosen from a $C_1$-$C_{30}$ alkyl; a —C(O)R moiety, or a —OR moiety, wherein R is a $C_1$-$C_{30}$ straight or branched chain alkyl group; and wherein said aryl groups may be substituted by a member selected from the group consisting of one to three halogen groups, a $C_1$-$C_8$ alkyl group, a $C_1$-$C_8$ alkoxy group, and combinations thereof.

24. A stabilizer composition according to embodiment 23, wherein the compound according to Formula (VIII) is a N,N-dihydrocarbylhydroxylamine wherein each of $T_1$ and $T_2$ is independently chosen from a member selected from the group consisting of benzyl, ethyl, octyl, lauryl, dodecyl, tetradecyl, hexadecyl, heptadecyl and octadecyl; or wherein each of $T_1$ and $T_2$ is the alkyl mixture found in hydrogenated tallow amine.

25. A stabilizer composition according to embodiment 23 or embodiment 24, wherein the compound according to Formula (VIII) is a N,N-dihydrocarbylhydroxylamine chosen from a member selected from the group consisting of N,N-dibenzylhydroxylamine; N,N-diethylhydroxylamine; N,N-dioctylhydroxylamine; N,N-dilaurylhydroxylamine; N,N-didodecylhydroxylamine; N,N-ditetradecylhydroxylaamine; N,N-dihexadecylhydroxylamine; N,N-dioctadecylhydroxylamine; N-hexadecyl-N-tetradecylhydroxylamine; N-hexadecyl-N-heptadecylhydroxylamine; N-hexadecyl-N-octadecylhydroxylamine; N-heptadecyl-N-octadecylhydroxylamine; and N,N-di(hydrogenated tallow)hydroxylamine.

26. A stabilizer composition according to any one of the preceding embodiments further comprising at least one compound chosen from a member selected from the group consisting of co-additives; tocopherol compounds; nucleating agents; fillers; reinforcing agents; polymer additives; and combinations thereof.

27. A stabilizer composition according to embodiment 26, wherein the tocopherol compound is chosen from a member selected from the group consisting of α-tocopherol, β-tocopherol, γ-tocopherol, δ-tocopherol, isomers thereof, related tocotrienols, and mixtures thereof.

28. A masterbatch composition comprising a stabilizer composition as defined in any one of embodiments 1-27, and an organic material identical to or compatible with an organic material to be stabilized.

29. A process for stabilizing an organic material subject to degradation and/or discoloration due to effects from light, oxygen, of heat, the process comprising:

adding a stabilizing amount of a stabilizer composition as defined in any one of embodiments 1-27, or of the masterbatch composition as defined in embodiment 28.

30. A process for enhancing the processing stability of an organic material, the process comprising adding before or during processing a stabilizing amount of a stabilizer composition as defined in any one of embodiments 1-27, or of the masterbatch composition as defined in embodiment 28.

30. A process for reducing or preventing discoloration of an organic material, the process comprising adding before or during processing a stabilizing amount of a stabilizer composition as defined in any one of embodiments 1-27, or of the masterbatch composition as defined in embodiment 28.

31. A process for producing a molded article, the process comprising adding a polymeric organic material and a polymer-stabilizing amount of a stabilizer composition as defined in any one of embodiments 1-27, or of the masterbatch composition as defined in embodiment 28 to a device or process for performing industrial molding; and cycling the stabilized polymeric organic material through the industrial molding process.

32. A process according to embodiment 31, wherein the industrial molding process or device is chosen from injection molding, rotomolding, blow molding, reel-to-reel molding, metal injection molding, compression molding, transfer molding, dip molding, gas assist molding, insert injection molding, micro molding, reaction injection molding, and two shot injection molding.

33. A process according to any one of embodiments 29-32, wherein the stabilizer composition is present from 0.001 to 65.0% by weight of the total weight of the organic material to be stabilized.

34. A process according to embodiment 33, wherein the stabilizer composition is present from 0.01 to 25% by weight of the total weight of the organic material to be stabilized.

35. A process according to embodiment 34, wherein the stabilizer composition is present from 0.01 to 10% by weight of the total weight of the organic material to be stabilized.

36. A process according to any one of embodiments 29-35, wherein the organic material to be stabilized is chosen from a member selected from the group consisting of polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, acrylonitrile-butadiene-styrene, styrene acrylonitrile, acrylate styrene acrylonitrile, cellulosic acetate butyrate, cellulosic polymers, polyimides, polyamideimides, polyetherimides, polyphenylsulfides, polyphenyloxidepolysulfones, polyethersulfones, polyvinylchlorides, polycarbonates, polyketones, aliphatic polyketones, thermoplastic olefins, aminoresin cross-linked polyacrylates and polyesters, polyisocyanate cross-linked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, fibers, waxes, and inks.

37. A process according to embodiment 36, wherein the organic material to be stabilized is a polyolefin polymer chosen from a member selected from the group consisting of i) polymers of monoolefins chosen from polypropylene, polyisobutylene, polybut-1-ene, and poly-4-methylpent-1-ene; ii) polymers of diolefins chosen from polyisoprene or polybutadiene; iii) polymers of cycloolefins chosen from cyclopentene, and norbornene; iv) polyethylene chosen from optionally crosslinked polyethylene, high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), very low density polyethylene (VLDPE), and ultralow density polyethylene (ULDPE); v) copolymers thereof; and vi) mixtures thereof.

38. A kit for stabilizing an organic material comprising in one or more containers a stabilizing amount of a stabilizer composition as defined in any one of embodiments 1-27.

39. A kit according to embodiment 38 further comprising in the same or additional container a co-additive.

40. A molded article:
   a) comprising a stabilizer composition as defined in any one of embodiments 1-27, or the masterbatch composition as defined in embodiment 28; or
   b) produced by a process according to any one of embodiments 31-37.

EXAMPLES

The following examples are provided to assist one skilled in the art to further understand certain embodiments of the present invention. These examples are intended for illustration purposes and are not to be construed as limiting the scope of the various embodiments of the present invention.

As a fluidity scale, melt index (hereinafter also referred to as MI) is industrially used predominantly for anticipating processability of an organic polymer material or for indication of standard and quality control. MI shows a flow rate in weight (unit: g) for 10 min when a high molecular weight polymer melted at a given temperature is extruded from a circular die having standard length and diameter by applying a certain load, and is used as an index of melt viscosity. Of the high molecular weight polymers, polypropylene having a lower MI value has better stability during processing, and that having a greater MI value has poor stability during processing. Polymer showing less variation in the values upon repeat measurements of MI is considered to have greater MI retention effect and to be superior in the stability during processing.

When an additive is kneaded into an organic polymer material (such as by multi-pass extrusion), the yellowness index (hereinafter also referred to as vi) is also widely used as a scale for evaluating discoloration of the polymer material. Yellowness index (YI) is measured by colorimeter, wherein a greater value means greater discoloration or color development and a smaller value means less coloring during processing, and therefore, superiority.

The superior advantages and unexpected properties provided by the stabilizer compositions and processes according to the present invention are now revealed by the following Examples taken in conjunction with the Figures.

Example 1

The rheological property of an organic polymer composition stabilized with a stabilizer composition according to the present invention is tested by multiple-pass extrusion.

FIG. 1A: A stabilizer composition according to the invention in the form of vitamin E acetate (0.15%) together with zinc stearate (0.05%) is dry blended with Profax 6301 polypropylene homopolymer (available from LyondellBasell Industries) (B), and compared to the polypropylene without any stabilizer additive composition (A). A Killion single screw extruder is set with a 60 mesh screen, 280° C. melt temperature, and a screw speed of 100 RPM. The blends are extruded 5 times (extruded and re-extruded 4 more times). Samples are collected after each pass and the melt-index determined. Samples from each pass are collected and the melt flow index is tested according to ASTM D1238-10 on a Dynisco melt indexer.

As indicated by the corresponding FIG. 1A, the results show that the polypropylene sample containing no stabilizer composition (A) could only be processed two times, whereas the polypropylene material blended with 0.15% vitamin E acetate was extruded 4 times.

Figure 1B:
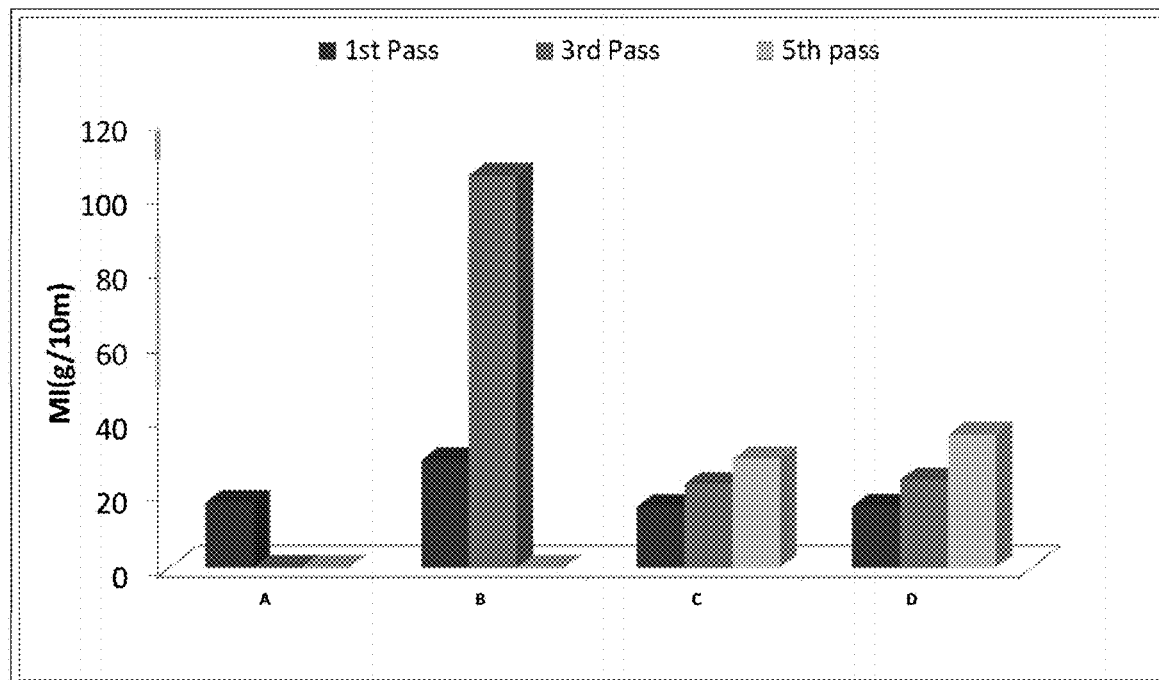

FIG. 1B: Polypropylene samples are prepared as described above and multi-pass extruded. (A): no stabilizing additive; (B): 0.15% vitamin E acetate; (C): 0.15% vitamin E; (D): 0.075% vitamin E and 0.075% vitamin E acetate. All samples containing stabilizing additive are also blended with 0.05% zinc stearate. As indicated by FIG. 1B, sample D shows better than expected performance based on the comparison samples A, B, or C.

Example 2

The mechanical properties of the organic materials (as determined by % elongation at break) are measured to see how the organic materials are affected by the processing. Two formulations are dry blended and compounded as in Example 1 with either no stabilizer additive (B) or vitamin E acetate at 0.15% together with 0.05% zinc stearate (C). The compounded material is extruded and then collected and compression molded into $\frac{1}{16}$" thick sheets. A sample of unprocessed polypropylene (A) is also compression molded in a $\frac{1}{16}$" sheet. Tensile samples are cut into dog-bone shaped specimens of type 5 (ASTM D638) using a punch press. Samples are tested on an MTS tensile tester at 2"/min crosshead speed. The median value of the five samples is used for all analyses. Using the unprocessed polypropylene as the baseline control, the percentage elongation retention of the polypropylene sample with and without a stabilizer composition according to the invention is calculated.

Figure 2:
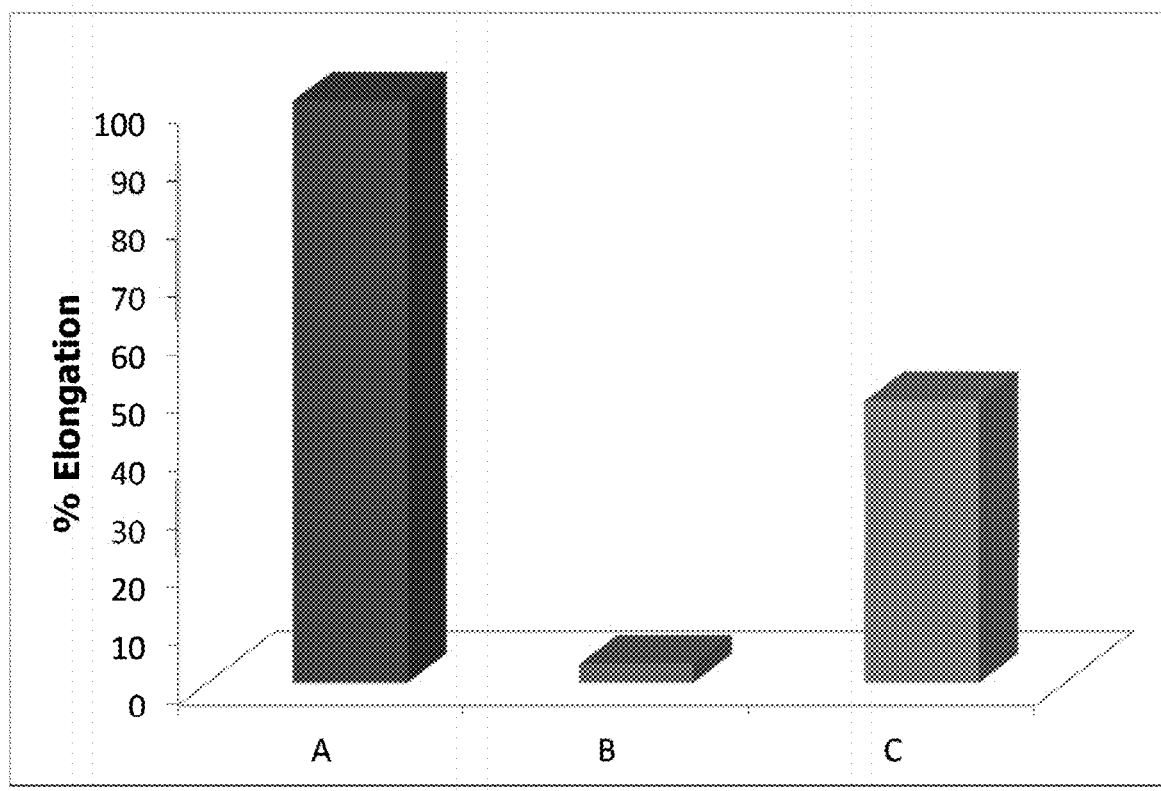
FIG. 2 illustrates the measurement of mechanical properties (as determined by percentage of retention of strain/elongation at break) of polypropylene resin formulated with (C) or without (B) a stabilizer composition according to the present invention and extruded one time, as compared to unprocessed (i.e., not extruded) polypropylene (A). Further experimental details are provided in Example 2 below.

As indicated by corresponding FIG. 2, sample (C) shows significant improvement in elongation retention compared to sample (B), as compared to unprocessed polypropylene resin (A).

Example 3

The Yellowness Index of organic polymer compositions with or without stabilizer compositions is measured for evaluating discoloration. Samples are prepared by dry blending stabilizing additives of the prior art or those according to the present invention at equal concentrations with low density polyethylene. Compounding is performed using a Killion single screw extruder set with a 60 mesh screen, 250° C. melt temperature, and a screw speed of 100 RPM. The samples are re-extruded 4 additional times (total of five). Samples of the compounded material are collected at each pass. Yellowness Index (ASTM E313) is determined using a Greta Macbeth Color i7, spectrophotometer. (A): no stabilizing additive; (B) 0.1% IRGANOX® 1010 phenolic antioxidant (available from BASF); (C): 0.1% CYANOX® 1790 phenolic antioxidant (available from Cytec Industries Inc.); (D) 0.1% vitamin E acetate. All samples containing stabilizing additive also contain 0.05% zinc stearate.

Figure 3:
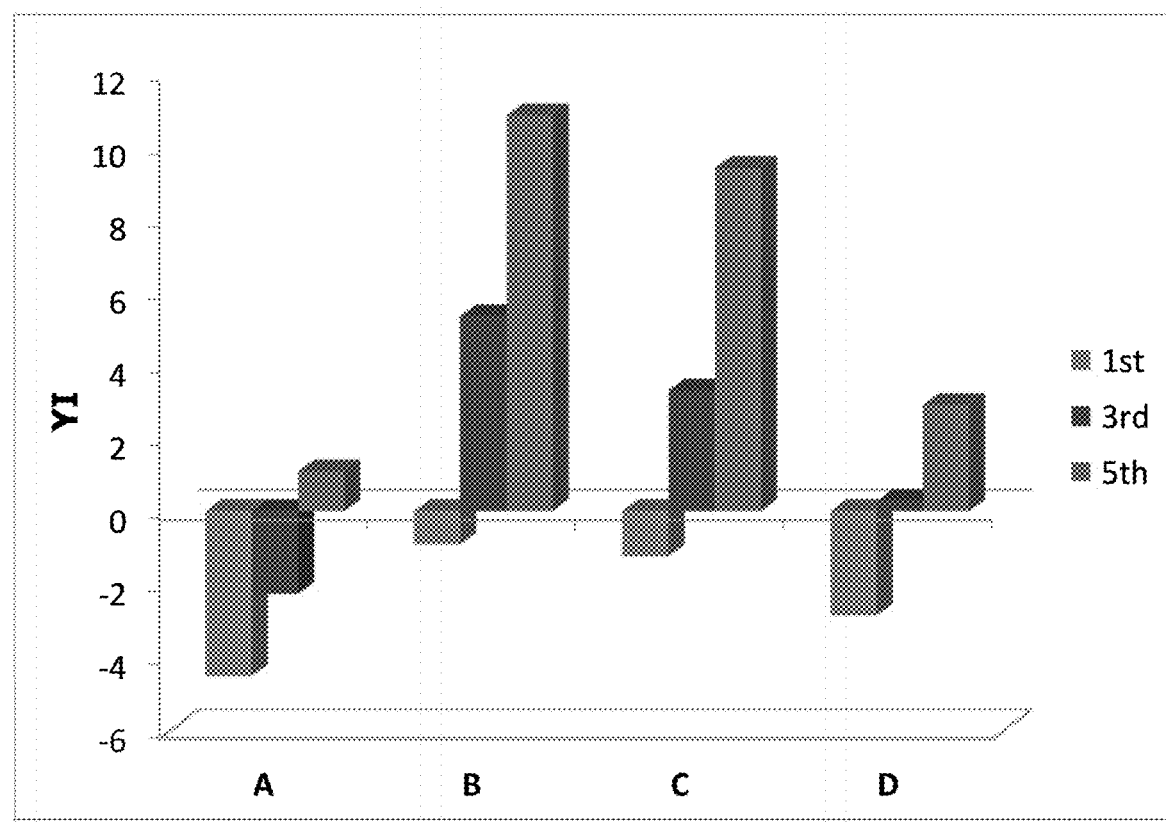
FIG. 3 illustrates the Yellowness Index of a low density polyethylene resin formulated with or without various stabilizer compositions, including those according to the present invention, and multi-pass extruded. (A): polyethylene resin multi-pass extruded without a stabilizing additive; (B): polyethylene resin multi-pass extruded with IRGANOX® 1010 (phenolic antioxidant); (C): polyethylene resin multi-pass extruded with CYANOX® 1790 (phenolic antioxidant); (D): polyethylene resin multi-pass extruded with vitamin E acetate according to the compositions and methods of the present invention. Further experimental details are provided in Example 3 below.

As indicated by corresponding FIG. 3, the Yellowness Index shows that samples (B) and (C) are more yellow (i.e., impart more color to the polyethylene) than (D), and that the delta for samples (B) and (C) significantly increases at the $3^{rd}$ and $5^{th}$ passes. The Yellowness Index for control sample (A) (no stabilizing additive) remains low because there is no stabilizing additive imparting color. Those of skill in the art would further appreciate and expect that the Yellowness Index for a polyethylene sample stabilized with only vitamin E would be even greater than samples (B) and (C), as it is known in the art that vitamin E badly discolors polymer substrates and that phenolic antioxidants such as IRGANOX® 1010 and CYANOX® 1790 reduce the undesired discoloring imparted by using vitamin E as a stabilizing additive.

Accordingly, the stabilizer compositions and processes according to the present invention provide unexpected and superior advantages to those stabilizer systems currently known and used. Taken together, these experiments show that organic materials stabilized with stabilizer systems according to the invention have improved mechanical and rheological properties, and that the stabilizer compositions according to the invention do not impart unfavorable color characteristics to the material to which it is added.

Various patent and/or scientific literature references have been referred to throughout this application. The disclosures of these publications in their entireties are hereby incorporated by reference as if written herein. In view of the above description and the examples, one of ordinary skill in the art will be able to practice the disclosure as claimed without undue experimentation.

Although the foregoing description has shown, described, and pointed out the fundamental novel features of the present teachings, it will be understood that various omissions, substitutions, and changes in the form of the detail of the apparatus as illustrated, as well as the uses thereof, may be made by those skilled in the art, without departing from the scope of the present teachings. Consequently, the scope of the present teachings should not be limited to the foregoing discussion, but should be defined by the appended claims.

What is claimed is:

1. A method for enhancing processing stability of polypropylene homopolymer, the method comprising adding to said polypropylene from 0.01% to 10% by weight based on the total weight of the polypropylene of a stabilizer composition comprising vitamin E acetate and zinc stearate; wherein amounts of the vitamin E acetate and zinc stearate in the stabilizer composition are selected to enhance processing stability of the polypropylene even in the absence of antistatic agents and organic phosphites and phosphonites by improving retention of melt index (MI) of the polypropylene when subjected to multi-pass extrusion.

2. A method according to claim 1, wherein the stabilizer composition further comprises at least one organic phosphite or phosphonite selected from the group consisting of triphenyl phosphite, diphenyl alkyl phosphites, phenyl dialkyl phosphites, trilauryl phosphite, trioctadecyl phosphite, distearyl pentaerythritol phosphite, tris(2,4-di-tert-butylphenyl) phosphite, tris(nonylphenyl) phosphite, a compound of formulae (A), (B), (C), (D), (E), (F), (G), (H), (J), (K) and (L):

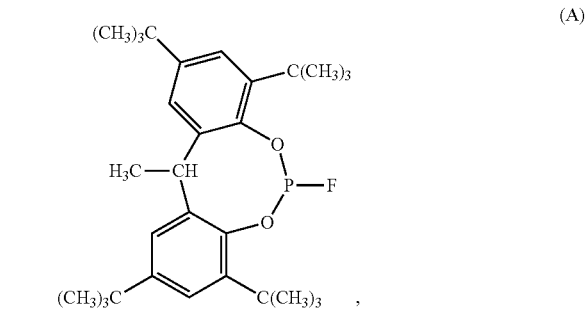

(A)

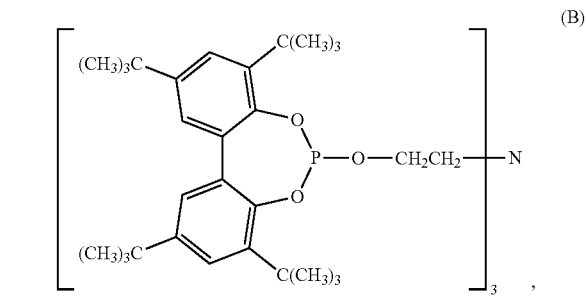

(B)

(C)

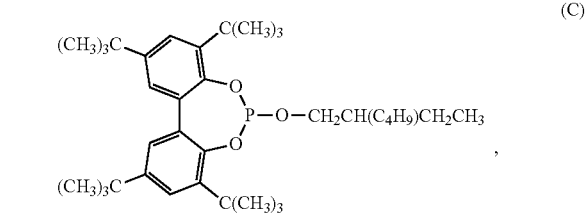

(D)

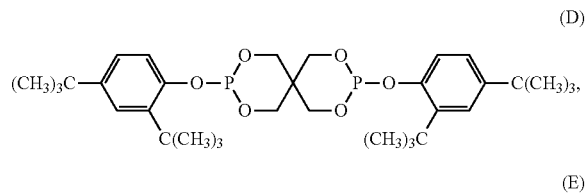

(E)

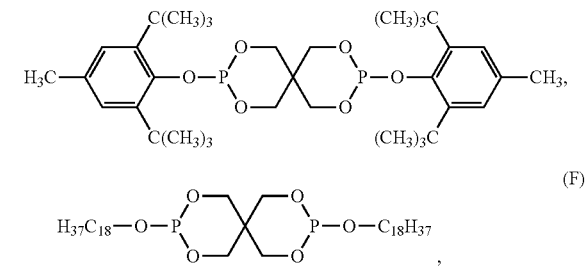

(F)

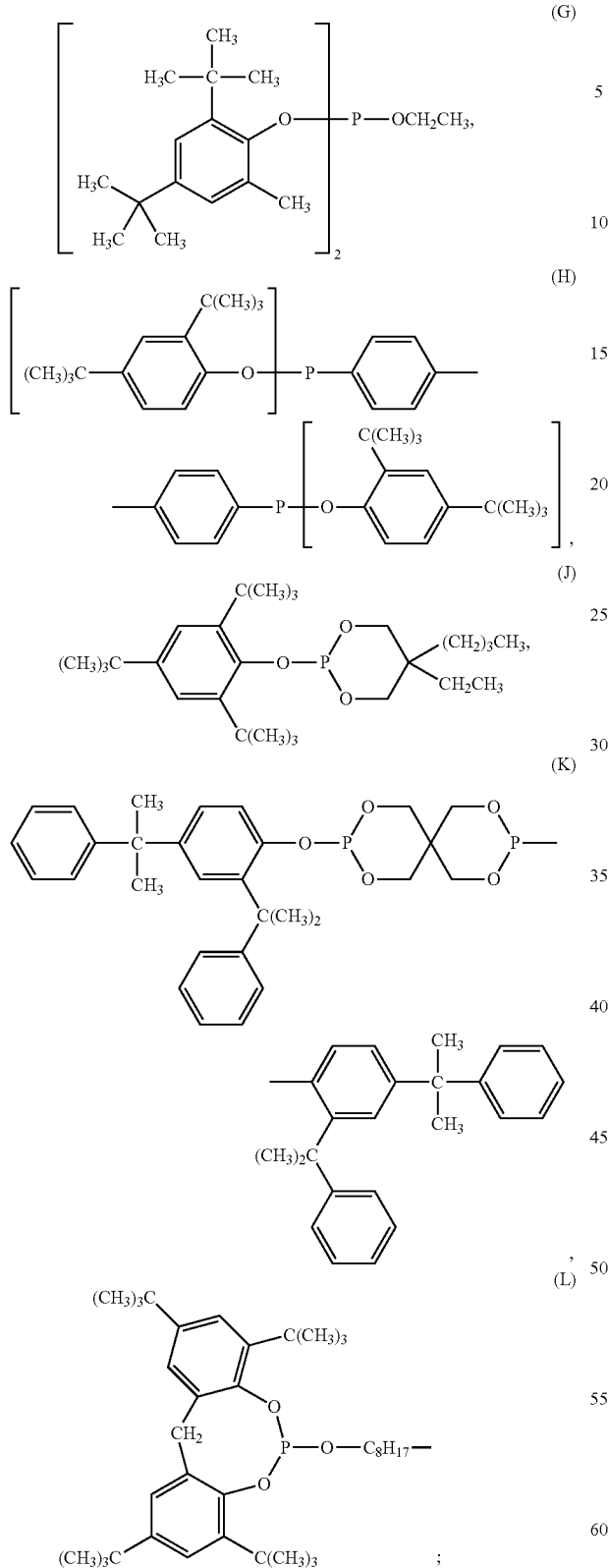

2-butyl-2-ethyl-1,3-propanediol 2,4,6-tri-t-butylphenol phosphite, bis-(2,6-di-t-butyl-4-methlphenyl) pentaerythritol diphosphite, 2-butyl-2-ethyl-1,3-propanediol 2,4-dicumylphenol phosphite, 2-butyl-2-ethyl-1,3-propanediol 4-methyl-2,6-di-t-butylphenol phosphite, and bis-(2,4,6-tri-t-butyl-phenyl) pentaerythritol diphosphite.

3. A method according to claim 1, wherein the stabilizer composition further comprises at least one hindered phenol compound having a molecular fragment according to one or more of Formula (IVa), (IVb), or (IVc):

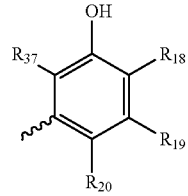

(IVa)

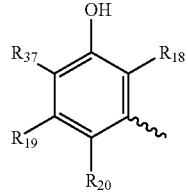

(IVb)

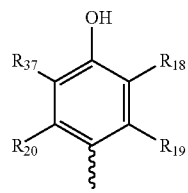

(IVc)

wherein:

$R_{18}$ in Formula (IVa), (IVb), and (IVc) is chosen from hydrogen or a $C_{1-4}$ hydrocarbyl;

each of $R_{19}$ and $R_{20}$ in Formula (IVa), (IVb), and (IVc) is independently chosen from hydrogen or a $C_1$-$C_{20}$ hydrocarbyl; and $R_{37}$ in Formula (IVa), (IVb), and (IVc) is chosen from a $C_1$-$C_{12}$ hydrocarbyl.

4. A method according to claim 3, wherein the at least one hindered phenol compound is selected from the group consisting of (1,3,5-tris(4-t-butyl-3-hydroxy-2,6-dimethylbenzyl)-1,3,5-triazine-2,4,6-(1H,3H,5H)-trione, 1,1,3-tris (2'-methyl-4'-hydroxy-5'-t-butylphenyl)butane, triethylene glycol bis[3-(3-t-butyl-4-hydroxy-5-methylphenyl)propionate], 4,4'-thiobis(2-t-butyl-5-methylphenol), 2,2'-thiodiethylene bis[3-(3-t-butyl-4-hydroxyl-5-methylphenyl)propionate], octadecyl 3-(3'-t-butyl-4'-hydroxy-5'-methylphenyl) propionate, tetrakismethylene(3-t-butyl-4-hydroxy-5-methylhydrocinnamate)methane, N,N'-hexamethylene bis [3-(3-t-butyl-4-hydroxy-5-methylphenyl)propionamide], di(4-tertiarybutyl-3-hydroxy-2,6-dimethyl benzyl) thiodipropionate, and octadecyl 3,5-di-(tert)-butyl-4-hydroxyhydrocinnamate.

5. A method according to claim 1, wherein the stabilizer composition further comprises a light stabilizer selected from the group consisting of hindered amine light stabilizers, hindered hydroxyl benzoates, nickel phenolates, ultraviolet light stabilizers, and combinations thereof.

6. A method according to claim 5, wherein the light stabilizer is a hindered amine light stabilizer compound comprising a molecular fragment according to:
(a) Formula (VI):

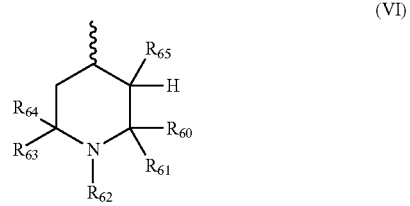

wherein:
  $R_{62}$ is selected from the group consisting of hydrogen, OH, $C_1$-$C_{20}$ hydrocarbyl, —$CH_2CN$, $C_1$-$C_{12}$ acyl, and $C_1$-$C_{18}$ alkoxy;
  $R_{65}$ is selected from the group consisting of hydrogen and $C_1$-$C_8$ hydrocarbyl; and
  each of $R_{60}$, $R_{61}$, $R_{63}$, and $R_{64}$ is independently chosen from a $C_1$-$C_{20}$ hydrocarbyl, or $R_{60}$ and $R_{61}$ and/or $R_{63}$ and $R_{64}$ taken together with the carbon to which they are attached form a $C_5$-$C_{10}$ cycloalkyl; or
(b) Formula (VIa)

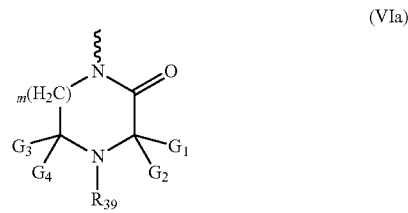

wherein:
  m is an integer from 1 to 2;
  $R_{39}$ is selected from the group consisting of hydrogen, OH, $C_1$-$C_{20}$ hydrocarbyl, —$CH_2CN$, $C_1$-$C_{12}$ acyl, and $C_1$-$C_{18}$ alkoxy; and
  each of $G_1$-$G_4$ is independently chosen from a $C_1$-$C_{20}$ hydrocarbyl.

7. A method according to claim 5, wherein the light stabilizer comprises an ultraviolet light absorber selected from the group consisting of a 2-hydroxybenzophenone compound, a 2-(2'-hydroxyphenyl)benzotriazole compound, a 2-(2'-hydroxyphenyl)-1,3,5-triazine compound, and combinations thereof.

8. A method according to claim 1, wherein the stabilizer composition further comprises at least one N,N-dihydrocarbylhydroxylamine selected from the group consisting of N,N-dibenzylhydroxylamine, N,N-diethylhydroxylamine, N,N-dioctylhydroxylamine, N,N-dilaurylhydroxylamine, N,N-didodecylhydroxylamine, N,N-ditetradecylhydroxylaamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, and N,N-di(hydrogenated tallow)hydroxylamine.

9. A method according to claim 1, wherein 0.15% of the vitamin E acetate and 0.05% of the zinc stearate are present based on the total weight of the polypropylene.

10. A method according to claim 1, wherein the stabilizer composition further comprises vitamin E.

11. A method according to claim 10, wherein 0.075% of the vitamin E acetate, 0.075% of the vitamin E, and 0.05% of the zinc stearate are present based on the total weight of the polypropylene.

12. A method according to claim 1, wherein the vitamin E acetate is a chroman-based compound according to Formula (Va):

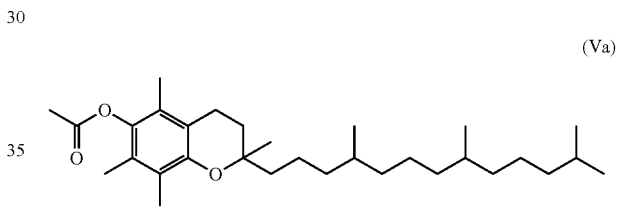

or isomers and/or mixtures thereof, including mixtures of said isomers.

13. A method according to claim 1, wherein the amounts of vitamin E acetate and zinc stearate are further selected to enhance processing stability of the polypropylene by improving elongation retention of the polypropylene when subjected to extrusion followed by compression molding.

* * * * *